(12) United States Patent
Oram et al.

(10) Patent No.: US 7,892,810 B2
(45) Date of Patent: Feb. 22, 2011

(54) CORYNEPHAGE INTEGRASE-BASED SITE-SPECIFIC INSERTION VECTOR SYSTEM

(75) Inventors: Diana M. Oram, Ellicott City, MD (US); Mark Oram, Ellicott City, MD (US); Joelle Woolston, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 463 days.

(21) Appl. No.: 11/901,013

(22) Filed: Sep. 14, 2007

(65) Prior Publication Data

US 2009/0197304 A1     Aug. 6, 2009

Related U.S. Application Data

(60) Provisional application No. 60/844,946, filed on Sep. 15, 2006.

(51) Int. Cl.
*C12N 9/00* (2006.01)
*C12N 1/20* (2006.01)
*C12N 15/00* (2006.01)
*C07H 21/04* (2006.01)

(52) U.S. Cl. ................. 435/252.3; 435/183; 435/320.1; 536/23.2

(58) Field of Classification Search ....................... None
See application file for complete search history.

(56) References Cited

U.S. PATENT DOCUMENTS 6,936,465 B1 *   8/2005   Katsumata et al. ....... 435/320.1

OTHER PUBLICATIONS

Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner*—Christian L Fronda
(74) *Attorney, Agent, or Firm*—Pratt & Associates, Inc; Sana A. Pratt

(57) ABSTRACT

The present invention provides a system for site-specific directed gene insertion of desired genes or foreign DNA into cellular genomes. The system includes novel vectors for integrating DNA into the genome of different hosts. Methods of using the vectors and transformed hosts are described.

37 Claims, 4 Drawing Sheets

Maps of integration vectors

Site-specific integration mediated by β-like phages

Siderophore Assays

SEQUENCE LISTING

```
<160> NUMBER OF SEQ ID NOS: 27

<210> SEQ ID NO 1
<211> LENGTH: 1370
<212> TYPE: DNA
<213> ORGANISM: Unknown
<220> FEATURE:
<223> OTHER INFORMATION: Corynephage b_int gene

<400> SEQUENCE: 1
gtgtaaagtg ggctgcagct aaccaatcac cttaaactga                          40
gcccgcctgc gctccgcctc tgacgcctca tgaactgtag                          80
acgcttcctc ggcacgtttc ctctcacttt ccatatgtgc                         120
ttccatcgcg ccgggaatgg catcaaggcc ttcttcccaa                         160
agatgtgcat agatatccag ggtcatcgca gcactggagt                         200
ggccgagcat gagttgtact gttttaacgt cagctcctgc                         240
tgcaatggcg atggatgcgg cagtgtggcg cagctcgtag                         280
gtgtcgaggt cgccaatccc agtccagatg cacaggtttt                         320
tccatacaac acgccagcgt gaggtggtcc atactttgcc                         360
tcgttcatct gggataagcc aggaatcagg atcttttcct                         400
tgagcgtagc gatcgaggag taacagaatt tcgccgccga                         440
tgggtacgtc gcggtggttt cgtgtttttg tcgagtcttc                         480
gtgtcctaag tcgtcgacgt cgcggcggat catgagacgt                         520
ccgcgtactg ggtctaggtc tttgactttg agtccttttg                         560
cttctcctgg tcttagaccg gtcatgatga ggacgcgtag                         600
gaggagtttt gcttgttcgg tgggtgcttg tctgatgagt                         640
tcgtcgactt ctgtgatttt gaggtagcgg cgttctgatt                         680
tcttttgttt tggtaggtcg ccagttctga tggggttttg                         720
gtggatgacg cctagctcca ctgcgaggtc gaggattccg                         760
tggatgatga ggccgacttt gcgcatggct gattcgctga                         800
```

-continued

| | |
|---|---|
| gtggtcgcgg tggttggctg gctggcacgc ctttcattgt | 840 |
| ggagagtgtg gggatccatg cgttgatgac tgagcgttgg | 880 |
| atgtgtgcgc aaggggtttg gccccattgt ggtcggatgt | 920 |
| ggacgttcca gtagctgagg tagtcgcgtt tggttttgtc | 960 |
| tgagatgttt ccttttgatg cgatccaggg ttcccatagg | 1000 |
| tcggagagtg tgatgtcgac tttgtctttg gtgatccagg | 1040 |
| tgccgtctgc ttttccgact tctgcgcggg ctgcccagag | 1080 |
| ttctgcctcg tcgcgggtct cgaatgtttt tgttgcttcg | 1120 |
| cgcccgttct caatccagac ggcttgccag cgcttgccga | 1160 |
| cgccccatcg cgctgatcgg atacgtttcg ttttggatgt | 1200 |
| ggtgttgggg tttcttttg tccagaggtc acggacggta | 1240 |
| gccatggggt agacttcttt cttgcttagt tctttagaag | 1280 |
| gggctgggca ttgcccttca ccgggtcttg cttgccggcg | 1320 |
| gacaggtgaa gggcacttgg ctgtctattg cttatgcaga | 1360 |
| gatctcacgg | 1370 |

<210> SEQ ID NO 2
<211> LENGTH: 421
<212> TYPE: DNA
<213> ORGANISM: Unknown
<220> FEATURE:
<223> OTHER INFORMATION: Corynephage b_attP region

<400> SEQUENCE: 2

| | |
|---|---|
| aggtgcatgc taagctatcg ctattttttg aaacaaaagc | 40 |
| tgaaaggtag tggggtcgtg tgccggtaag ccgaacggtt | 80 |
| ccggaatggc gctatagtat gcacaggtag agcagaattc | 120 |
| gaatctgact acggatcaga aggttggggg ttcgaatccc | 160 |
| tccgggcgca caagtgaaac cccagctcat agcatgtttg | 200 |
| agctggggtt tcttcatggc gtgtgggttg tctgactgtt | 240 |
| ggctgttgtt gcaggtggtt ggtgctcgta ccgaacgcat | 280 |
| accgaacata ggccgaacag aaaccgaaca agagtcgaac | 320 |
| gggcaccgaa cggggtaatt cccatagatc agtttctgcg | 360 |
| tcccttgtag gtaagatgat cacttatggg tgaactcgac | 400 |
| acagctgacc tgcagttaga a | 421 |

<210> SEQ ID NO 3
<211> LENGTH: 150
<212> TYPE: DNA
<213> ORGANISM: Unknown
<220> FEATURE:
<223> OTHER INFORMATION: Corynebacteria _attB site

<400> SEQUENCE: 3

| | |
|---|---|
| tgaaacttgc gcccgtagct caacggatag agcatctgac | 40 |
| tacggatcag aaggttgggg gttcgaatcc ctccgggcgc | 80 |
| acaagttaaa ccccagctca cagaatgtgt gggctggggt | 120 |
| ttcttcgtgc ttgcggtgcg ctggcgcccc | 150 |

<210> SEQ ID NO 4
<211> LENGTH: 24
<212> TYPE: DNA
<213> ORGANISM: Artificial sequence
<220> FEATURE:
<223> OTHER INFORMATION: primer _-INT-PstI

<400> SEQUENCE: 4
gtgtaaagtg ggctgcagct aacc                                          24

<210> SEQ ID NO 5
<211> LENGTH: 25
<212> TYPE: DNA
<213> ORGANISM: Artificial sequence
<220> FEATURE:
<223> OTHER INFORMATION: primer _-INT-BglIII

<400> SEQUENCE: 5
cgtgagatct ctgcataagc aatag                                         25

<210> SEQ ID NO 6
<211> LENGTH: 33
<212> TYPE: DNA
<213> ORGANISM: Artificial sequence
<220> FEATURE:
<223> OTHER INFORMATION: primer ATTP-UP-SphI

<400> SEQUENCE: 6
aggtgcatgc taagctatcg ctattttttg aaa                                33

<210> SEQ ID NO 7
<211> LENGTH: 30
<212> TYPE: DNA
<213> ORGANISM: Artificial sequence
<220> FEATURE:
<223> OTHER INFORMATION: primer ATTP-DN-PstI

<400> SEQUENCE: 7
ttctaactgc aggtcagctg tgtcgagttc                                    30

<210> SEQ ID NO 8
<211> LENGTH: 4425
<212> TYPE: DNA
<213> ORGANISM: Artificial sequence
<220> FEATURE:
<223> OTHER INFORMATION: pKMO3W

<400> SEQUENCE: 8
ctaagctatc gctattttt  gaaacaaaag ctgaaaggta                          40
gtggggtcgt gtgccggtaa gccgaacggt tccggaatgg                          80
cgctatagta tgcacaggta gagcagaatt cgaatctgac                         120
tacggatcag aaggttgggg gttcgaatcc ctccgggcgc                         160
acaagtgaaa ccccagctca tagcatgttt gagctggggt                         200
ttcttcatgg cgtgtgggtt gtctgactgt tggctgttgt                         240
tgcaggtggt tggtgctcgt accgaacgca taccgaacat                         280
aggccgaaca gaaaccgaac aagagtcgaa cgggcaccga                         320
acggggtaat tcccatagat cagtttctgc gtcccttgta                         360
ggtaagatga tcacttatgg gtgaactcga cacagctgac                         400

-continued

| | |
|---|---|
| ctgcagctaa ccaatcacct taaactgagc ccgcctgcgc | 440 |
| tccgcctctg acgcctcatg aactgtagac gcttcctcgg | 480 |
| cacgtttcct ctcactttcc atatgtgctt ccatcgcgcc | 520 |
| gggaatggca tcaaggcctt cttcccaaag atgtgcatag | 560 |
| atatccaggg tcatcgcagc actggagtgg ccgagcatga | 600 |
| gttgtactgt tttaacgtca gctcctgctg caatggcgat | 640 |
| ggatgcggca gtgtggcgca gctcgtaggt gtcgaggtcg | 680 |
| ccaatcccag tccagatgca caggttttc catacaacac | 720 |
| gccagcgtga ggtggtccat actttgcctc gttcatctgg | 760 |
| gataagccag gaatcaggat cttttccttg agcgtagcga | 800 |
| tcgaggagta acagaatttc gccgccgatg ggtacgtcgc | 840 |
| ggtggtttcg tgttttgtc gagtcttcgt gtcctaagtc | 880 |
| gtcgacgtcg cggcggatca tgagacgtcc gcgtactggg | 920 |
| tctaggtctt tgactttgag tccttttgct tctcctggtc | 960 |
| ttagaccggt catgatgagg acgcgtagga ggagttttgc | 1000 |
| ttgttcggtg ggtgcttgtc tgatgagttc gtcgacttct | 1040 |
| gtgattttga ggtagcggcg ttctgatttc ttttgttttg | 1080 |
| gtaggtcgcc agttctgatg gggttttggt ggatgacgcc | 1120 |
| tagctccact gcgaggtcga ggattccgtg gatgatgagg | 1160 |
| ccgactttgc gcatggctga ttcgctgagt ggtcgcggtg | 1200 |
| gttggctggc tggcacgcct tcattgtgg agagtgtggg | 1240 |
| gatccatgcg ttgatgactg agcgttggat gtgtgcgcaa | 1280 |
| ggggtttggc cccattgtgg tcggatgtgg acgttccagt | 1320 |
| agctgaggta gtcgcgtttg gttttgtctg agatgtttcc | 1360 |
| ttttgatgcg atccagggtt cccataggtc ggagagtgtg | 1400 |
| atgtcgactt tgtctttggt gatccaggtg ccgtctgctt | 1440 |
| ttccgacttc tgcgcgggct gcccagagtt ctgcctcgtc | 1480 |
| gcgggtctcg aatgtttttg ttgcttcgcg cccgttctca | 1520 |
| atccagacgg cttgccagcg cttgccgacg ccccatcgcg | 1560 |
| ctgatcggat acgtttcgtt ttggatgtgg tgttggggtt | 1600 |
| tcttttgtc cagaggtcac ggacggtagc catggggtag | 1640 |
| acttctttct tgcttagttc tttagaaggg gctgggcatt | 1680 |
| gcccttcacc gggtcttgct tgccggcgga caggtgaagg | 1720 |
| gcacttggct gtctattgct tatgcagaga tcccccgggta | 1760 |
| ccgagctcga attcactggc cgtcgtttta caacgtcgtg | 1800 |
| actgggaaaa ccctggcgtt acccaactta atcgccttgc | 1840 |
| agcacatccc cctttcgcca gctggcgtaa tagcgaagag | 1880 |
| gcccgcaccg atcgcccttc ccaacagttg cgcagcctga | 1920 |
| atggcgaatg gcgcctgatg cggtattttc tccttacgca | 1960 |
| tctgtgcggt atttcacacc gcatatggtg cactctcagt | 2000 |

| | |
|---|---|
| acaatctgct ctgatgccgc atagttaagc cagccccgac | 2040 |
| acccgccaac acccgctgac gcgccctgac gggcttgtct | 2080 |
| gctcccggca tccgcttaca gacaagctgt gaccgtctcc | 2120 |
| gggagctgca tgtgtcagag gttttcaccg tcatcaccga | 2160 |
| aacgcgcgag acgaaagggc ctcgtgatac gcctattttt | 2200 |
| ataggttaat gtcatgataa taatggtttc ttagacgtca | 2240 |
| ggtggcactt ttcggggaaa tgtgcgcgga acccctattt | 2280 |
| gtttattttt ctaaatacat tcaaatatgt atccgctcat | 2320 |
| gagacaataa ccctgataaa tgcttcaata atctagataa | 2360 |
| aaatatatca tcatgaacaa taaaactgtc tgcttacata | 2400 |
| aacagtaata caaggggtgt tatgagccat attcaacggg | 2440 |
| aaacgtcttg ctcgaggccg cgattaaatt ccaacatgga | 2480 |
| tgctgattta tatgggtata aatgggctcg cgataatgtc | 2520 |
| gggcaatcag gtgcgacaat ctatcgattg tatgggaagc | 2560 |
| ccgatgcgcc agagttgttt ctgaaacatg gcaaaggtag | 2600 |
| cgttgccaat gatgttacag atgagatggt cagactaaac | 2640 |
| tggctgacgg aatttatgcc tcttccgacc atcaagcatt | 2680 |
| ttatccgtac tcctgatgat gcatggttac tcaccactgc | 2720 |
| gatccccgga aaaacagcat tccaggtatt agaagaatat | 2760 |
| cctgattcag gtgaaaatat tgttgatgcg ctggcagtgt | 2800 |
| tcctgcgccg gttgcattcg attcctgttt gtaattgtcc | 2840 |
| ttttaacagc gatcgcgtat ttcgtctcgc tcaggcgcaa | 2880 |
| tcacgaatga ataacggttt ggttgatgcg agtgattttg | 2920 |
| atgacgagcg taatggctgg cctgttgaac aagtctggaa | 2960 |
| agaaatgcat aaacttttgc cattctcacc ggattcagtc | 3000 |
| gtcactcatg gtgatttctc acttgataac cttatttttg | 3040 |
| acgaggggaa attaataggt tgtattgatg ttggacgagt | 3080 |
| cggaatcgca gaccgatacc aggatcttgc catcctatgg | 3120 |
| aactgcctcg gtgagttttc tccttcatta cagaaacggc | 3160 |
| tttttcaaaa atatggtatt gataatcctg atatgaataa | 3200 |
| attgcagttt catttgatgc tcgatgagtt tttctaatca | 3240 |
| gaattggtta attggttgta acactggcaa agctttacgc | 3280 |
| tgaaaacttc attttttaatt taaaaggatc taggtgaaga | 3320 |
| tcctttttga taatctcatg accaaaatcc cttaacgtga | 3360 |
| gttttcgttc cactgagcgt cagacccgt agaaaagatc | 3400 |
| aaaggatctt cttgagatcc ttttttttctg cgcgtaatct | 3440 |
| gctgcttgca aacaaaaaaa ccaccgctac cagcggtggt | 3480 |
| ttgtttgccg gatcaagagc taccaactct ttttccgaag | 3520 |
| gtaactggct tcagcagagc gcagatacca aatactgtcc | 3560 |

| | |
|---|---|
| ttctagtgta gccgtagtta ggccaccact tcaagaactc | 3600 |
| tgtagcaccg cctacatacc tcgctctgct aatcctgtta | 3640 |
| ccagtggctg ctgccagtgg cgataagtcg tgtcttaccg | 3680 |
| ggttggactc aagacgatag ttaccggata aggcgcagcg | 3720 |
| gtcgggctga acgggggtt cgtgcacaca gcccagcttg | 3760 |
| gagcgaacga cctacaccga actgagatac ctacagcgtg | 3800 |
| agctatgaga aagcgccacg cttcccgaag ggagaaaggc | 3840 |
| ggacaggtat ccggtaagcg gcagggtcgg aacaggagag | 3880 |
| cgcacgaggg agcttccagg gggaaacgcc tggtatcttt | 3920 |
| atagtcctgt cgggtttcgc cacctctgac ttgagcgtcg | 3960 |
| atttttgtga tgctcgtcag gggggcggag cctatggaaa | 4000 |
| aacgccagca acgcggcctt tttacggttc ctggccttt | 4040 |
| gctggccttt tgctcacatg ttctttcctg cgttatcccc | 4080 |
| tgattctgtg gataaccgta ttaccgcctt tgagtgagct | 4120 |
| gataccgctc gccgcagccg aacgaccgag cgcagcgagt | 4160 |
| cagtgagcga ggaagcggaa gagcgcccaa tacgcaaacc | 4200 |
| gcctctcccc gcgcgttggc cgattcatta atgcagctgg | 4240 |
| cacgacaggt ttcccgactg gaaagcgggc agtgagcgca | 4280 |
| acgcaattaa tgtgagttag ctcactcatt aggcacccca | 4320 |
| ggctttacac tttatgcttc cggctcgtat gttgtgtgga | 4360 |
| attgtgagcg gataacaatt tcacacagga aacagctatg | 4400 |
| accatgatta cgccaagctt gcatg | 4425 |

```
<210> SEQ ID NO 9
<211> LENGTH: 6845
<212> TYPE: DNA
<213> ORGANISM: Artificial sequence
<220> FEATURE:
<223> OTHER INFORMATION: pKM03W+mob

<400> SEQUENCE: 9
```

| | |
|---|---|
| cgagctcgaa ttcactggcc gtcgttttac aacgtcgtga | 40 |
| ctgggaaaac cctggcgtta cccaacttaa tcgccttgca | 80 |
| gcacatcccc ctttcgccag ctggcgtaat agcgaagagg | 120 |
| cccgcaccga tcgcccttcc caacagttgc gcagcctgaa | 160 |
| tggcgaatgg cgcctgatgc ggtattttct ccttacgcat | 200 |
| ctgtgcggta tttcacaccg catatggtgc actctcagta | 240 |
| caatctgctc tgatgccgca tagttaagcc agccccgaca | 280 |
| cccgccaaca cccgctgacg cgccctgacg ggcttgtctg | 320 |
| ctcccggcat ccgcttacag acaagctgtg accgtctccg | 360 |
| ggagctgcat gtgtcagagg ttttcaccgt catcaccgaa | 400 |
| acgcgcgaga cgaaagggcc tcgtgatacg cctatttttta | 440 |
| taggttaatg tcatgataat aatggtttct tagacgtcag | 480 |
| gtggcacttt tcggggaaat gtgcgcggaa cccctatttg | 520 |

```
tttattttc   taaatacatt   caaatatgta   tccgctcatg                     560
agacaataac   cctgataaat   gcttcaataa   tctagataaa                    600
aatatatcat   catgaacaat   aaaactgtct   gcttacataa                    640
acagtaatac   aagggtgtt    atgagccata   ttcaacggga                    680
aacgtcttgc   tcgaggccgc   gattaaattc   caacatggat                    720
gctgatttat   atgggtataa   atgggctcgc   gataatgtcg                    760
ggcaatcagg   tgcgacaatc   tatcgattgt   atgggaagcc                    800
cgatgcgcca   gagttgtttc   tgaaacatgg   caaaggtagc                    840
gttgccaatg   atgttacaga   tgagatggtc   agactaaact                    880
ggctgacgga   atttatgcct   cttccgacca   tcaagcattt                    920
tatccgtact   cctgatgatg   catggttact   caccactgcg                    960
atccccggaa   aaacagcatt   ccaggtatta   agaatatc                      1000 ctgattcagg   tgaaaatatt   gttgatgcgc   tggcagtgtt                    1040
cctgcgccgg   ttgcattcga   ttcctgtttg   taattgtcct                    1080
tttaacagcg   atcgcgtatt   tcgtctcgct   caggcgcaat                    1120
cacgaatgaa   taacggtttg   gttgatgcga   gtgattttga                    1160
tgacgagcgt   aatggctggc   ctgttgaaca   agtctggaaa                    1200
gaaatgcata   aacttttgcc   attctcaccg   gattcagtcg                    1240
tcactcatgg   tgatttctca   cttgataacc   ttattttga                     1280 cgagggaaa    ttaataggtt   gtattgatgt   tggacgagtc                    1320
ggaatcgcag   accgatacca   ggatcttgcc   atcctatgga                    1360
actgcctcgg   tgagttttct   ccttcattac   agaaacggct                    1400
ttttcaaaaa   tatggtattg   ataatcctga   tatgaataaa                    1440
ttgcagtttc   atttgatgct   cgatgagttt   ttctaatcag                    1480
aattggttaa   ttggttgtaa   cactggcaaa   gctttacgct                    1520
gaaaacttca   tttttaattt   aaaaggatct   aggtgaagat                    1560
cctttttgat   aatctcatga   ccaaaatccc   ttaacgtgag                    1600
ttttcgttcc   actgagcgtc   agaccccgta   gaaaagatca                    1640
aaggatcttc   ttgagatcct   ttttttctgc   gcgtaatctg                    1680
ctgcttgcaa   acaaaaaaac   caccgctacc   agcggtggtt                    1720
tgtttgccgg   atcaagagct   accaactctt   tttccgaagg                    1760
taactggctt   cagcagagcg   cagataccaa   atactgtcct                    1800
tctagtgtag   ccgtagttag   gccaccactt   caagaactct                    1840
gtagcaccgc   ctacatacct   cgctctgcta   atcctgttac                    1880
cagtggctgc   tgccagtggc   gataagtcgt   gtcttaccgg                    1920
gttggactca   agacgatagt   taccggataa   ggcgcagcgg                    1960
tcgggctgaa   cggggggttc   gtgcacacag   cccagcttgg                    2000
agcgaacgac   ctacaccgaa   ctgagatacc   tacagcgtga                    2040
gctatgagaa   agcgccacgc   ttcccgaagg   gagaaaggcg                    2080
```

| | |
|---|---|
| gacaggtatc cggtaagcgg cagggtcgga acaggagagc | 2120 |
| gcacgaggga gcttccaggg ggaaacgcct ggtatcttta | 2160 |
| tagtcctgtc gggtttcgcc acctctgact tgagcgtcga | 2200 |
| ttttgtgat gctcgtcagg ggggcggagc ctatggaaaa | 2240 |
| acgccagcaa cgcggccttt ttacggttcc tggcctttg | 2280 |
| ctggcctttt gctcacatgt tctttcctgc gttatcccct | 2320 |
| gattctgtgg ataaccgtat taccgccttt gagtgagctg | 2360 |
| ataccgctcg ccgcagccga acgaccgagc gcagcgagtc | 2400 |
| agtgagcgag gaagcggaag agcgcccaat acgcaaaccg | 2440 |
| cctctccccg cgcgttggcc gattcattaa tgcagctggc | 2480 |
| acgacaggtt tcccgactgg aaagcgggca gtgagcgcaa | 2520 |
| cgcaattaat gtgagttagc tcactcatta ggcaccccag | 2560 |
| gctttacact ttatgcttcc ggctcgtatg ttgtgtggaa | 2600 |
| ttgtgagcgg ataacaattt cacacaggaa acagctatga | 2640 |
| ccatgattac gccaagcttg catgctaagc tatcgctatt | 2680 |
| ttttgaaaca aaagctgaaa ggtagtgggg tcgtgtgccg | 2720 |
| gtaagccgaa cggttccgga atggcgctat agtatgcaca | 2760 |
| ggtagagcag aattcgaatc tgactacgga tcagaaggtt | 2800 |
| gggggttcga atccctccgg gcgcacaagt gaaaccccag | 2840 |
| ctcatagcat gtttgagctg gggtttcttc atggcgtgtg | 2880 |
| ggttgtctga ctgttggctg ttgttgcagg tggttggtgc | 2920 |
| tcgtaccgaa cgcataccga acataggccg aacagaaacc | 2960 |
| gaacaagagt cgaacgggca ccgaacgggg taattcccat | 3000 |
| agatcagttt ctgcgtccct tgtaggtaag atgatcactt | 3040 |
| atgggtgaac tcgacacagc tgacctgcag ctaaccaatc | 3080 |
| accttaaact gagcccgcct gcgctccgcc tctgacgcct | 3120 |
| catgaactgt agacgcttcc tcggcacgtt tcctctcact | 3160 |
| ttccatatgt gcttccatcg cgccgggaat ggcatcaagg | 3200 |
| ccttcttccc aaagatgtgc atagatatcc agggtcatcg | 3240 |
| cagcactgga gtggccgagc atgagttgta ctgttttaac | 3280 |
| gtcagctcct gctgcaatgg cgatggatgc ggcagtgtgg | 3320 |
| cgcagctcgt aggtgtcgag gtcgccaatc ccagtccaga | 3360 |
| tgcacaggtt tttccataca acacgccagc gtgaggtggt | 3400 |
| ccatactttg cctcgttcat ctgggataag ccaggaatca | 3440 |
| ggatcttttc cttgagcgta gcgatcgagg agtaacagaa | 3480 |
| tttcgccgcc gatgggtacg tcgcggtggt ttcgtgtttt | 3520 |
| tgtcgagtct tcgtgtccta agtcgtcgac gtcgcggcgg | 3560 |
| atcatgagac gtccgcgtac tgggtctagg tctttgactt | 3600 |
| tgagtccttt tgcttctcct ggtcttagac cggtcatgat | 3640 |
| gaggacgcgt aggaggagtt ttgcttgttc ggtgggtgct | 3680 |

```
tgtctgatga gttcgtcgac ttctgtgatt ttgaggtagc              3720
ggcgttctga tttcttttgt tttggtaggt cgccagttct              3760
gatggggttt tggtggatga cgcctagctc cactgcgagg              3800
tcgaggattc cgtggatgat gaggccgact ttgcgcatgg              3840
ctgattcgct gagtggtcgc ggtggttggc tggctggcac              3880
gcctttcatt gtggagagtg tggggatcca tgcgttgatg              3920
actgagcgtt ggatgtgtgc gcaaggggtt tggccccatt              3960
gtggtcggat gtggacgttc cagtagctga ggtagtcgcg              4000
tttggttttg tctgagatgt ttccttttga tgcgatccag              4040
ggttcccata ggtcggagag tgtgatgtcg actttgtctt              4080
tggtgatcca ggtgccgtct gcttttccga cttctgcgcg              4120
ggctgcccag agttctgcct cgtcgcgggt ctcgaatgtt              4160
tttgttgctt cgcgcccgtt ctcaatccag acggcttgcc              4200
agcgcttgcc gacgcccat cgcgctgatc ggatacgttt              4240
cgttttggat gtggtgttgg ggtttctttt tgtccagagg              4280
tcacggacgg tagccatggg gtagacttct ttcttgctta              4320
gttctttaga aggggctggg cattgcccctt caccgggtct             4360
tgcttgccgg cggacaggtg aagggcactt ggctgtctat              4400
tgcttatgca gagatccccg ggtaccgagc gaaatgaccg              4440
accaagcgac gcccaacctg ccatcacgag atttcgattc              4480
caccgccgcc ttctatgaaa ggttgggctt cggaatcgtt              4520
ttccgggacg ccctcgcgga cgtgctcata gtccacgacg              4560
cccgtgattt tgtagccctg gccgacggcc agcaggtagg              4600
ccgacaggct catgccggcc gccgccgcct tttcctcaat              4640
cgctcttcgt tcgtctggaa ggcagtacac cttgataggt              4680
gggctgccct tcctggttgg cttggtttca tcagccatcc              4720
gcttgccctc atctgttacg ccggcggtag ccggccagcc              4760
tcgcagagca ggattcccgt tgagcaccgc caggtgcgaa              4800
taagggacag tgaagaagga acaccccgctc gcgggtgggc             4840
ctacttcacc tatcctgccc cgctgacgcc gttggataca              4880
ccaaggaaag tctacacgaa ccctttggca aaatcctgta               4920
tatcgtgcga aaaggatgg atataccgaa aaaatcgcta               4960
taatgacccc gaagcagggt tatgcagcgg aaaagcgctg               5000
cttccctgct gttttgtgga atatctaccg actggaaaca               5040
ggcaaatgca ggaaattact gaactgaggg gacaggcgag               5080
agacgatgcc aaagagctcc tgaaaatctc gataactcaa               5120
aaaatacgcc cggtagtgat cttatttcat tatggtgaaa               5160
gttggaacct cttacgtgcc gatcaacgtc tcattttcgc               5200
caaaagttgg cccagggctt cccggtatca acagggacac              5240
```

```
caggatttat ttattctgcg aagtgatctt ccgtcacagg              5280
tatttattcg gcgcaaagtg cgtcgggtga tgctgccaac              5320
ttactgattt agtgtatgat ggtgtttttg aggtgctcca              5360
gtggcttctg tttctatcag ctcctgaaaa tctcgataac              5400
tcaaaaaata cgcccggtag tgatcttatt tcattatggt              5440
gaaagttgga acctcttacg tgccgatcaa cgtctcattt              5480
tcgccaaaag ttggcccagg gcttcccggt atcaacaggg              5520
acaccaggat ttatttattc tgcgaagtga tcttccgtca              5560
caggtattta ttcggcgcaa agtgcgtcgg gtgatgctgc              5600
caacttactg atttagtgta tgatggtgtt tttgaggtgc              5640
tccagtggct tctgtttcta tcagggctgg atgatcctcc              5680
agcgcgggga tctcatgctg gagttcttcg cccaccccaa              5720
aaggatctag gtgaagatcc ttttttgataa tctcatgacc             5760 aaaatccctt aacgtgagtt tcgttccac tgagcgtcag               5800 accccgtaga aagatcaaa ggatcttctt gagatccttt                5840
ttttctgcgc gtaatctgct gcttgcaaac aaaaaaacca              5880
ccgctaccag cggtggtttg tttgccggat caagagctac              5920
caactctttt tccgaaggta actggcttca gcagagcgca              5960
gataccaaat actgtccttc tagtgtagcc gtagttaggc              6000
caccacttca agaactctgt agcaccgcct acatacctcg              6040
ctctgctaat cctgttacca gtggctgctg ccagtggcga              6080
taagtcgtgt cttaccgggt tggactcaag acgatagtta              6120
ccggataagg cgcagcggtc gggctgaacg gggggttcgt              6160
gcacacagcc cagcttggag cgaacgacct acaccgaact              6200
gagataccta cagcgtgagc attgagaaag cgccacgctt              6240
cccgaaggga gaaaggcgga caggtatccg gtaagcggca              6280
gggtcggaac aggagagcgc acgagggagc ttccaggggg              6320
aaacgcctgg tatctttata gtcctgtcgg gtttcgccac              6360
ctctgacttg agcgtcgatt tttgtgatgc tcgtcagggg              6400
ggcggagcct atggaaaaac gccagcaacg cggccttttt              6440
acggttcctg gccttttgct ggccttttgc tcacatgttc              6480
tttcctgcgt tatcccctga ttctgtggat aaccgtatta              6520
ccgcctttga gtgagctgat accgctcgcc gcagccgaac              6560
gaccgagcgc agcgagtcag tgagcgagga agcggaagag              6600
cgcccaatac gcaaaccgcc tctccccgcg cgttggccga              6640
ttcattaatg cagctggcac gacaggtttc ccgactggaa              6680
agcgggcagt gagcgcaacg caattaatgt gagttagctc              6720
actcattagg caccccaggc tttacacttt atgcttccgg              6760
ctcgtatgtt gtgtggaatt gtgagcggat aacaatttca              6800
cacaggaaac agctatgacc atgattacga attcgagctc              6840
``` ggtac 6845

<210> SEQ ID NO 10
<211> LENGTH: 5092
<212> TYPE: DNA
<213> ORGANISM: Artificial sequence
<220> FEATURE:
<223> OTHER INFORMATION: pK-AIM

<400> SEQUENCE: 10

| | |
|---|---:|
| cgaattcact ggccgtcgtt ttacaacgtc gtgactggga | 40 |
| aaaccctggc gttacccaac ttaatcgcct tgcagcacat | 80 |
| ccccctttcg ccagctggcg taatagcgaa gaggcccgca | 120 |
| ccgatcgccc ttcccaacag ttgcgcagcc tgaatggcga | 160 |
| atggcgcctg atgcggtatt ttctccttac gcatctgtgc | 200 |
| ggtatttcac accgcatatg gtgcactctc agtacaatct | 240 |
| gctctgatgc cgcatagtta agccagcccc gacacccgcc | 280 |
| aacacccgct gacgcgccct gacgggcttg tctgctcccg | 320 |
| gcatccgctt acagacaagc tgtgaccgtc tccgggagct | 360 |
| gcatgtgtca gaggttttca ccgtcatcac cgaaacgcgc | 400 |
| gagacgaaag ggcctcgtga tacgcctatt tttataggtt | 440 |
| aatgtcatga taataatggt ttcttagacg tcaggtggca | 480 |
| cttttcgggg aaatgtgcgc ggaaccccta tttgtttatt | 520 |
| tttctaaata cattcaaata tgtatccgct catgagacaa | 560 |
| taaccctgat aaatgcttca ataatctaga taaaaatata | 600 |
| tcatcatgaa caataaaact gtctgcttac ataaacagta | 640 |
| atacaagggg tgttatgagc catattcaac gggaaacgtc | 680 |
| ttgctcgagg ccgcgattaa attccaacat ggatgctgat | 720 |
| ttatatgggt ataaatgggc tcgcgataat gtcgggcaat | 760 |
| caggtgcgac aatctatcga ttgtatggga agcccgatgc | 800 |
| gccagagttg tttctgaaac atggcaaagg tagcgttgcc | 840 |
| aatgatgtta cagatgagat ggtcagacta aactggctga | 880 |
| cggaatttat gcctcttccg accatcaagc attttatccg | 920 |
| tactcctgat gatgcatggt tactcaccac tgcgatcccc | 960 |
| ggaaaaacag cattccaggt attagaagaa tatcctgatt | 1000 |
| caggtgaaaa tattgttgat gcgctggcag tgttcctgcg | 1040 |
| ccggttgcat tcgattcctg tttgtaattg tccttttaac | 1080 |
| agcgatcgcg tatttcgtct cgctcaggcg caatcacgaa | 1120 |
| tgaataacgg tttggttgat gcgagtgatt ttgatgacga | 1160 |
| gcgtaatggc tggcctgttg aacaagtctg gaaagaaatg | 1200 |
| cataaacttt tgccattctc accggattca gtcgtcactc | 1240 |
| atggtgattt ctcacttgat aaccttattt ttgacgaggg | 1280 |
| gaaattaata ggttgtattg atgttggacg agtcggaatc | 1320 |

```
gcagaccgat accaggatct tgccatccta tggaactgcc              1360
tcggtgagtt ttctccttca ttacagaaac ggcttttttca             1400 aaaatatggt attgataatc ctgatatgaa taaattgcag              1440
tttcatttga tgctcgatga gttttttctaa tcagaattgg             1480 ttaattggtt gtaacactgg caaagcttta cgctgaaaac              1520 ttcatttta atttaaaagg atctaggtga agatcctttt               1560
tgataatctc atgaccaaaa tcccttaacg tgagttttcg              1600
ttccactgag cgtcagaccc cgtagaaaag atcaaaggat              1640
cttcttgaga tcctttttt ctgcgcgtaa tctgctgctt               1680
gcaaacaaaa aaaccaccgc taccagcggt ggtttgtttg              1720
ccggatcaag agctaccaac tcttttccg aaggtaactg                1760 gcttcagcag agcgcagata ccaaatactg tccttctagt              1800
gtagccgtag ttaggccacc acttcaagaa ctctgtagca              1840
ccgcctacat acctcgctct gctaatcctg ttaccagtgg              1880
ctgctgccag tggcgataag tcgtgtctta ccgggttgga               1920
ctcaagacga tagttaccgg ataaggcgca gcggtcgggc              1960
tgaacggggg gttcgtgcac acagcccagc ttggagcgaa              2000
cgacctacac cgaactgaga tacctacagc gtgagctatg              2040
agaaagcgcc acgcttcccg aagggagaaa ggcggacagg              2080
tatccggtaa gcggcagggt cggaacagga gagcgcacga              2120
gggagcttcc agggggaaac gcctggtatc tttatagtcc              2160
tgtcgggttt cgccacctct gacttgagcg tcgattttg                2200 tgatgctcgt cagggggggcg gagcctatgg aaaaacgcca              2240
gcaacgcggc cttttttacgg ttcctggcct tttgctggcc              2280
ttttgctcac atgttctttc ctgcgttatc ccctgattct               2320
gtggataacc gtattaccgc ctttgagtga gctgataccg               2360
ctcgccgcag ccgaacgacc gagcgcagcg agtcagtgag               2400
cgaggaagcg gaaagagcgcc caatacgcaa accgcctctc              2440
cccgcgcgtt ggccgattca ttaatgcagc tggcacgaca              2480
ggtttcccga ctggaaagcg ggcagtgagc gcaacgcaat               2520
taatgtgagt tagctcactc attaggcacc ccaggcttta              2560
cactttatgc ttccggctcg tatgttgtgt ggaattgtga               2600
gcggataaca atttcacaca ggaaacagct atgaccatga               2640
ttacgccaag cttgcatgct aagctatcgc tatttttga                2680 aacaaaagct gaaggtagt gggtcgtgt gccggtaagc                 2720 cgaacggttc cggaatggcg ctatagtatg cacaggtaga               2760
gcagaattcg aatctgacta cggatcagaa ggttgggggt               2800
tcgaatccct ccgggcgcac aagtgaaacc ccagctcata               2840
gcatgtttga gctggggttt cttcatggcg tgtgggttgt               2880
ctgactgttg gctgttgttg caggtggttg gtgctcgtac               2920
```

```
cgaacgcata ccgaacatag gccgaacaga aaccgaacaa       2960
gagtcgaacg ggcaccgaac ggggtaattc ccatagatca       3000
gtttctgcgt cccttgtagg taagatgatc acttatgggt       3040
gaactcgaca cagctgacct gcagctaacc aatcacctta       3080
aactgagccc gcctgcgctc cgcctctgac gcctcatgaa       3120
ctgtagacgc ttcctcggca cgtttcctct cactttccat       3160
atgtgcttcc atcgcgccgg gaatggcatc aaggccttct       3200
tcccaaagat gtgcatagat atccagggtc atcgcagcac       3240
tggagtggcc gagcatgagt tgtactgttt taacgtcagc       3280
tcctgctgca atggcgatgg atgcggcagt gtggcgcagc       3320
tcgtaggtgt cgaggtcgcc aatcccagtc cagatgcaca       3360 ggttttttcca tacaacacgc cagcgtgagg tggtccatac      3400
tttgcctcgt tcatctggga taagccagga atcaggatct       3440
tttccttgag cgtagcgatc gaggagtaac agaatttcgc       3480
cgccgatggg tacgtcgcgg tggtttcgtg tttttgtcga       3520
gtcttcgtgt cctaagtcgt cgacgtcgcg gcggatcatg       3560
agacgtccgc gtactgggtc taggtctttg actttgagtc       3600
cttttgcttc tcctggtctt agaccggtca tgatgaggac       3640
gcgtaggagg agttttgctt gttcggtggg tgcttgtctg       3680
atgagttcgt cgacttctgt gattttgagg tagcggcgtt       3720
ctgatttctt ttgttttggt aggtcgccag ttctgatggg       3760
gttttggtgg atgacgccta gctccactgc gaggtcgagg       3800
attccgtgga tgatgaggcc gactttgcgc atggctgatt       3840
cgctgagtgg tcgcggtggt tggctggctg gcacgccttt       3880
cattgtggag agtgtgggga tccatgcgtt gatgactgag       3920
cgttggatgt gtgcgcaagg ggtttggccc cattgtggtc       3960
ggatgtggac gttccagtag ctgaggtagt cgcgtttggt       4000
tttgtctgag atgtttcctt ttgatgcgat ccagggttcc       4040
cataggtcgg agagtgtgat gtcgactttg tctttggtga       4080
tccaggtgcc gtctgctttt ccgacttctg cgcgggctgc       4120
ccagagttct gcctcgtcgc gggtctcgaa tgttttttgtt      4160 gcttcgcgcc cgttctcaat ccagacggct tgccagcgct       4200
tgccgacgcc ccatcgcgct gatcggatac gtttcgtttt       4240
ggatgtggtg ttgggggtttc ttttttgtcca gaggtcacgg     4280 acggtagcca tggggtagac ttctttcttg cttagttctt       4320
tagaaggggc tgggcattgc ccttcaccgg gtcttgcttg       4360
ccggcggaca ggtgaagggc acttggctgt ctattgctta       4400
tgcagagatc cccgggtacc gagcgaaatg accgaccaag       4440
cgacgcccaa cctgccatca cgagatttcg attccaccgc       4480
```

-continued

```
cgccttctat gaaaggttgg gcttcggaat cgttttccgg         4520
gacgccctcg cggacgtgct catagtccac gacgcccgtg         4560
attttgtagc cctggccgac ggccagcagg taggccgaca         4600
ggctcatgcc ggccgccgcc gccttttcct caatcgctct         4640
tcgttcgtct ggaaggcagt acaccttgat aggtgggctg         4680
cccttcctgg ttggcttggt ttcatcagcc atccgcttgc         4720
cctcatctgt tacgccggcg gtagccggcc agcctcgcag         4760
agcaggattc ccgttgagca ccgccaggtg cgaataaggg         4800
acagtgaaga aggaacaccc gctcgcgggt gggcctactt         4840
cacctatcct gccccgctga cgccgttgga tacaccaagg         4880
aaagtctaca cgaaccctt ggcaaaatcc tgtatatcgt          4920
gcgaaaaagg atggatatac cgaaaaaatc gctataatga         4960
ccccgaagca gggttatgca gcggaaaagc gctgcttccc         5000
tgctgttttg tggaatatct accgactgga aacaggcaaa         5040
tgcaggaaat tactgaactg aggggacagg cgagagacga         5080
tgccaaagag ct                                      5092
```

<210> SEQ ID NO 11
<211> LENGTH: 34
<212> TYPE: DNA
<213> ORGANISM: Artificial sequence
<220> FEATURE:
<223> OTHER INFORMATION: oligo dtxR-SacI-UP

<400> SEQUENCE: 11

```
gccgaaaaac ttgagctcta cgcacaataa agcg              34
```

<210> SEQ ID NO 12
<211> LENGTH: 31
<212> TYPE: DNA
<213> ORGANISM: Artificial sequence
<220> FEATURE:
<223> OTHER INFORMATION: oligo dtxR-SacI-DN

<400> SEQUENCE: 12

```
catctaattt cgagctcttt aatatttaga g                 31
```

<210> SEQ ID NO 13
<211> LENGTH: 49
<212> TYPE: DNA
<213> ORGANISM: Artificial sequence
<220> FEATURE:
<223> OTHER INFORMATION: oligo polylinker 1

<400> SEQUENCE: 13

```
cttaattaac gttaactagt agatctgggc ccgcggcgg         40 ccgcacgtg                                          49
```

<210> SEQ ID NO 14
<211> LENGTH: 57
<212> TYPE: DNA
<213> ORGANISM: Artificial sequence
<220> FEATURE:
<223> OTHER INFORMATION: oligo polylinker 2

<400> SEQUENCE: 14

| | |
|---|---|
| aattcacgtg cggccgccgc ggggcccaga tctactagtt | 40 |
| aacgttaatt aagagct | 57 |

<210> SEQ ID NO 15
<211> LENGTH: 5139
<212> TYPE: DNA
<213> ORGANISM: Artificial sequence
<220> FEATURE:
<223> OTHER INFORMATION: pK-PIM

<400> SEQUENCE: 15

| | |
|---|---|
| aattcactgg ccgtcgtttt acaacgtcgt gactgggaaa | 40 |
| accctggcgt tacccaactt aatcgccttg cagcacatcc | 80 |
| cccttcgcc agctggcgta atagcgaaga ggcccgcacc | 120 |
| gatcgccctt cccaacagtt gcgcagcctg aatggcgaat | 160 |
| ggcgcctgat gcggtatttt ctccttacgc atctgtgcgg | 200 |
| tatttcacac cgcatatggt gcactctcag tacaatctgc | 240 |
| tctgatgccg catagttaag ccagccccga cacccgccaa | 280 |
| cacccgctga cgcgccctga cgggcttgtc tgctcccggc | 320 |
| atccgcttac agacaagctg tgaccgtctc cgggagctgc | 360 |
| atgtgtcaga ggttttcacc gtcatcaccg aaacgcgcga | 400 |
| gacgaaaggg cctcgtgata cgcctatttt tataggttaa | 440 |
| tgtcatgata taatggttt cttagacgtc aggtggcact | 480 |
| tttcggggaa atgtgcgcgg aacccctatt tgtttatttt | 520 |
| tctaaataca ttcaaatatg tatccgctca tgagacaata | 560 |
| accctgataa atgcttcaat aatctagata aaaatatatc | 600 |
| atcatgaaca ataaaactgt ctgcttacat aaacagtaat | 640 |
| acaaggggtg ttatgagcca tattcaacgg gaaacgtctt | 680 |
| gctcgaggcc gcgattaaat tccaacatgg atgctgattt | 720 |
| atatgggtat aaatgggctc gcgataatgt cgggcaatca | 760 |
| ggtgcgacaa tctatcgatt gtatgggaag cccgatgcgc | 800 |
| cagagttgtt tctgaaacat ggcaaaggta gcgttgccaa | 840 |
| tgatgttaca gatgagatgg tcagactaaa ctggctgacg | 880 |
| gaatttatgc ctcttccgac catcaagcat tttatccgta | 920 |
| ctcctgatga tgcatggtta ctcaccactg cgatccccgg | 960 |
| aaaaacagca ttccaggtat tagaagaata tcctgattca | 1000 |
| ggtgaaaata ttgttgatgc gctggcagtg ttcctgcgcc | 1040 |
| ggttgcattc gattcctgtt tgtaattgtc cttttaacag | 1080 |
| cgatcgcgta tttcgtctcg ctcaggcgca atcacgaatg | 1120 |
| aataacggtt tggttgatgc gagtgatttt gatgacgagc | 1160 |
| gtaatggctg gcctgttgaa caagtctgga agaaatgca | 1200 |
| taaactttg ccattctcac cggattcagt cgtcactcat | 1240 |
| ggtgatttct cacttgataa ccttattttt gacgagggga | 1280 |

```
aattaatagg ttgtattgat gttggacgag tcggaatcgc      1320
agaccgatac caggatcttg ccatcctatg gaactgcctc      1360
ggtgagtttt ctccttcatt acagaaacgg cttttttcaaa     1400 aatatggtat tgataatcct gatatgaata aattgcagtt      1440
tcatttgatg ctcgatgagt ttttctaatc agaattggtt      1480
aattggttgt aacactggca aagctttacg ctgaaaactt      1520 cattttttaat ttaaaaggat ctaggtgaag atccttttg      1560 ataatctcat gaccaaaatc ccttaacgtg agttttcgtt      1600
ccactgagcg tcagaccccg tagaaaagat caaaggatct      1640
tcttgagatc ctttttttct gcgcgtaatc tgctgcttgc      1680
aaacaaaaaa accaccgcta ccagcggtgg tttgtttgcc      1720
ggatcaagag ctaccaactc tttttccgaa ggtaactggc      1760
ttcagcagag cgcagatacc aaatactgtc cttctagtgt      1800
agccgtagtt aggccaccac ttcaagaact ctgtagcacc      1840
gcctacatac ctcgctctgc taatcctgtt accagtggct      1880
gctgccagtg gcgataagtc gtgtcttacc gggttggact      1920
caagacgata gttaccggat aaggcgcagc ggtcgggctg      1960
aacggggggt tcgtgcacac agcccagctt ggagcgaacg      2000
acctacaccg aactgagata cctacagcgt gagctatgag      2040
aaagcgccac gcttcccgaa gggagaaagg cggacaggta      2080
tccggtaagc ggcagggtcg gaacaggaga gcgcacgagg      2120
gagcttccag ggggaaacgc ctggtatctt tatagtcctg      2160
tcgggtttcg ccacctctga cttgagcgtc gatttttgtg      2200
atgctcgtca gggggggcgga gcctatggaa aaacgccagc     2240
aacgcggcct ttttacggtt cctggccttt tgctggcctt      2280
ttgctcacat gttctttcct gcgttatccc ctgattctgt      2320
ggataaccgt attaccgcct ttgagtgagc tgataccgct      2360
cgccgcagcc gaacgaccga gcgcagcgag tcagtgagcg      2400
aggaagcgga agagcgccca atacgcaaac cgcctctccc      2440
cgcgcgttgg ccgattcatt aatgcagctg gcacgacagg      2480
tttcccgact ggaaagcggg cagtgagcgc aacgcaatta      2520
atgtgagtta gctcactcat taggcacccc aggctttaca      2560
ctttatgctt ccggctcgta tgttgtgtgg aattgtgagc      2600
ggataacaat ttcacacagg aaacagctat gaccatgatt      2640
acgccaagct tgcatgctaa gctatcgcta tttttttgaaa     2680 caaaagctga aggtagtgg ggtcgtgtgc cggtaagccg       2720
aacggttccg gaatggcgct atagtatgca caggtagagc      2760
agaattcgaa tctgactacg gatcagaagg ttgggggttc      2800
gaatccctcc gggcgcacaa gtgaaacccc agctcatagc      2840
atgtttgagc tggggtttct tcatggcgtg tgggttgtct      2880
```

```
gactgttggc tgttgttgca ggtggttggt gctcgtaccg       2920
aacgcatacc gaacataggc cgaacagaaa ccgaacaaga       2960
gtcgaacggg caccgaacgg ggtaattccc atagatcagt       3000
ttctgcgtcc cttgtaggta agatgatcac ttatgggtga       3040
actcgacaca gctgacctgc agctaaccaa tcaccttaaa       3080
ctgagcccgc ctgcgctccg cctctgacgc ctcatgaact       3120
gtagacgctt cctcggcacg tttcctctca ctttccatat       3160
gtgcttccat cgcgccggga atggcatcaa ggccttcttc       3200
ccaaagatgt gcatagatat ccagggtcat cgcagcactg       3240
gagtggccga gcatgagttg tactgtttta acgtcagctc       3280
ctgctgcaat ggcgatggat gcggcagtgt ggcgcagctc       3320
gtaggtgtcg aggtcgccaa tcccagtcca gatgcacagg       3360
tttttccata caacacgcca gcgtgaggtg gtccatactt       3400
tgcctcgttc atctgggata agccaggaat caggatcttt       3440
tccttgagcg tagcgatcga ggagtaacag aatttcgccg       3480
ccgatgggta cgtcgcggtg gtttcgtgtt tttgtcgagt       3520
cttcgtgtcc taagtcgtcg acgtcgcggc ggatcatgag       3560
acgtccgcgt actgggtcta ggtctttgac tttgagtcct       3600
tttgcttctc ctggtcttag accggtcatg atgaggacgc       3640
gtaggaggag ttttgcttgt tcggtgggtg cttgtctgat       3680
gagttcgtcg acttctgtga ttttgaggta gcggcgttct       3720
gatttctttt gttttggtag gtcgccagtt ctgatggggt       3760
tttggtggat gacgcctagc tccactgcga ggtcgaggat       3800
tccgtggatg atgaggccga cttttgcgcat ggctgattcg      3840 ctgagtggtc gcggtggttg gctggctggc acgcctttca       3880
ttgtggagag tgtggggatc catgcgttga tgactgagcg       3920
ttggatgtgt gcgcaagggg tttggcccca ttgtggtcgg       3960
atgtggacgt tccagtagct gaggtagtcg cgtttggttt       4000
tgtctgagat gttttcttttt gatgcgatcc agggttccca      4040
taggtcggag agtgtgatgt cgactttgtc tttggtgatc       4080
caggtgccgt ctgctttttcc gacttctgcg cgggctgccc      4120
agagttctgc ctcgtcgcgg gtctcgaatg tttttgttgc       4160
ttcgcgcccg ttctcaatcc agacggcttg ccagcgcttg       4200
ccgacgcccc atcgcgctga tcggatacgt ttcgttttgg       4240
atgtggtgtt ggggtttctt tttgtccaga ggtcacggac       4280
ggtagccatg gggtagactt cttttcttgct tagttcttta      4320 gaaggggctg ggcattgccc ttcaccgggt cttgcttgcc       4360
ggcggacagg tgaagggcac ttggctgtct attgcttatg       4400
cagagatccc cgggtaccga gcgaaatgac cgaccaagcg       4440
```

| | |
|---|---|
| acgcccaacc tgccatcacg agatttcgat tccaccgccg | 4480 |
| ccttctatga aaggttgggc ttcggaatcg ttttccggga | 4520 |
| cgccctcgcg gacgtgctca tagtccacga cgcccgtgat | 4560 |
| tttgtagccc tggccgacgg ccagcaggta ggccgacagg | 4600 |
| ctcatgccgg ccgccgccgc cttttcctca atcgctcttc | 4640 |
| gttcgtctgg aaggcagtac accttgatag gtgggctgcc | 4680 |
| cttcctggtt ggcttggttt catcagccat ccgcttgccc | 4720 |
| tcatctgtta cgccggcggt agccggccag cctcgcagag | 4760 |
| caggattccc gttgagcacc gccaggtgcg aataagggac | 4800 |
| agtgaagaag gaacacccgc tcgcgggtgg gcctacttca | 4840 |
| cctatcctgc cccgctgacg ccgttggata caccaaggaa | 4880 |
| agtctacacg aacccttttgg caaaatcctg tatatcgtgc | 4920 |
| gaaaaaggat ggatataccg aaaaaatcgc tataatgacc | 4960 |
| ccgaagcagg gttatgcagc ggaaaagcgc tgcttccctg | 5000 |
| ctgttttgtg gaatatctac cgactggaaa caggcaaatg | 5040 |
| caggaaatta ctgaactgag gggacaggcg agagacgatg | 5080 |
| ccaaagagct cttaattaac gttaactagt agatctgggc | 5120 |
| cccgcggcgg ccgcacgtg | 5139 |

```
<210> SEQ ID NO 16
<211> LENGTH: 33
<212> TYPE: DNA
<213> ORGANISM: Artificial sequence
<220> FEATURE:
<223> OTHER INFORMATION: primer ATTP-UP

<400> SEQUENCE: 16
```

| | |
|---|---|
| aggtgcatgc taagctatcg ctattttttg aaa | 33 |

```
<210> SEQ ID NO 17
<211> LENGTH: 30
<212> TYPE: DNA
<213> ORGANISM: Artificial sequence
<220> FEATURE:
<223> OTHER INFORMATION: primer ATTP-DN

<400> SEQUENCE: 17
```

| | |
|---|---|
| ttctaactgc aggtcagctg tgtcgagttc | 30 |

```
<210> SEQ ID NO 18
<211> LENGTH: 25
<212> TYPE: DNA
<213> ORGANISM: Artificial sequence
<220> FEATURE:
<223> OTHER INFORMATION: primer ATTB1-UP

<400> SEQUENCE: 18
```

| | |
|---|---|
| ggctcaatct gatcggcgtg gtgct | 25 |

```
<210> SEQ ID NO 19
<211> LENGTH: 26
<212> TYPE: DNA
<213> ORGANISM: Artificial sequence
<220> FEATURE:
<223> OTHER INFORMATION: primer ATTB1-DN
```

```
<400> SEQUENCE: 19
ggcgagtagg cacgcagcaa gaaaaa                                    26

<210> SEQ ID NO 20
<211> LENGTH: 29
<212> TYPE: DNA
<213> ORGANISM: Artificial sequence
<220> FEATURE:
<223> OTHER INFORMATION: primer ATTB2-UP

<400> SEQUENCE: 20
cgtacgtcgg gatctgggaa aggtggtct                                 29

<210> SEQ ID NO 21
<211> LENGTH: 25
<212> TYPE: DNA
<213> ORGANISM: Artificial sequence
<220> FEATURE:
<223> OTHER INFORMATION: primer ATTB2-DN

<400> SEQUENCE: 21
cgaagactct agtgtaatcg gtgta                                     25

<210> SEQ ID NO 22
<211> LENGTH: 30
<212> TYPE: DNA
<213> ORGANISM: Artificial sequence
<220> FEATURE:
<223> OTHER INFORMATION: oligo ATTB1g-UP

<400> SEQUENCE: 22
ctgaacatca tcgcagtcat cctcattacg                                30

<210> SEQ ID NO 23
<211> LENGTH: 22
<212> TYPE: DNA
<213> ORGANISM: Artificial sequence
<220> FEATURE:
<223> OTHER INFORMATION: oligo ATTB1g-DN

<400> SEQUENCE: 23
cggcgcacgg atcgaagtgt tc                                        22

<210> SEQ ID NO 24
<211> LENGTH: 30
<212> TYPE: DNA
<213> ORGANISM: Artificial sequence
<220> FEATURE:
<223> OTHER INFORMATION: oligo attB2g-UP

<400> SEQUENCE: 24
cataagtagg gatagttgcc aaatctgctc                                30

<210> SEQ ID NO 25
<211> LENGTH: 30
<212> TYPE: DNA
<213> ORGANISM: Artificial sequence
<220> FEATURE:
<223> OTHER INFORMATION: oligo ATTB2g-DN

<400> SEQUENCE: 25
tgtcgagaaa cgaatgcccc agtttcaccc                                30

<210> SEQ ID NO 26
```

-continued

```
<211> LENGTH: 21
<212> TYPE: DNA
<213> ORGANISM: Artificial sequence
<220> FEATURE:
<223> OTHER INFORMATION: oligo ATTBu-UP

<400> SEQUENCE: 26
ccacctatgc gcccgtagct c                                              21

<210> SEQ ID NO 27
<211> LENGTH: 24
<212> TYPE: DNA
<213> ORGANISM: Artificial sequence
<220> FEATURE:
<223> OTHER INFORMATION: oligo ATTBu-DN

<400> SEQUENCE: 27
caacaatcca ccaaccaaac acac                                           24
```

CORYNEPHAGE INTEGRASE-BASED SITE-SPECIFIC INSERTION VECTOR SYSTEM

Figure 1:
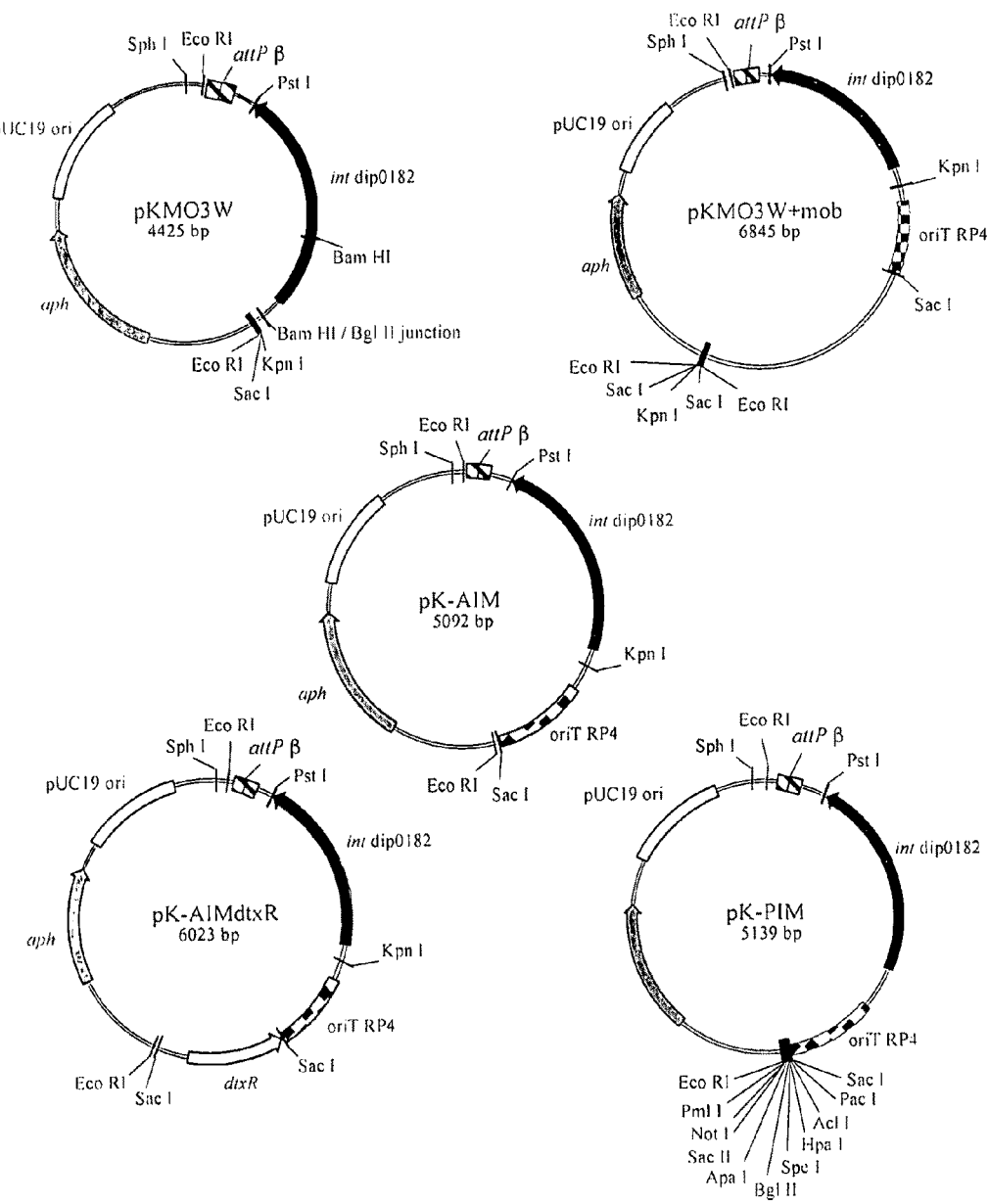

This application claims benefit of priority from Provisional Application Ser. No. 60/844,946 filed on Sep. 15, 2006.

This invention was funded by the National Institutes of Health. The Government has certain rights in the invention pursuant to NIH/NIAID grant No. K22 AI60882.

Corynebacterium diphtheriae is a human pathogen and the causative agent of diphtheria. While all C. diphtheriae strains are capable of colonizing humans, only those that produce diphtheria toxin (DT) cause the life-threatening toxin-mediated manifestations of the disease (Holmes, R. K., 2000, J. Infect. Dis. 181 Suppl. 1, S156-167). Immunization with formaldehyde-treated DT leads to induction of a protective antitoxic immune response to diphtheria, although antitoxin levels wane over time and periodic re-immunization is required to maintain immunity. Diphtheria continues to pose a significant health threat both in certain sub-tropical and tropical countries where C. diphtheriae is endemic and in areas where a significant proportion of the population lacks or has failed to maintain full immunity. Indeed, loss of protective levels of antitoxin in the adult population was one major contributing factor to the diphtheria epidemic in the 1990's in the former Soviet Union (Golaz et al., 2000, J. Infect. Dis. 181, Suppl 1, S237-243; Mattos-Guaraldi et al., 2003, Mem. Inst. Oswaldo Cruz 98, 987-993).

The tox gene encoding DT is carried on various temperate corynephages, such as β, which integrate into the C. diphtheriae chromosome during the lysogenic phase of the infective cycle (Holmes, 2000, supra). The expression of tox in lysogens is regulated by the chromosomally-encoded dtxR gene product in response to $Fe^{2+}$ levels (Schmitt and Holmes, 1991, Infect. Immun. 59, 1899-1904; Boyd et al., 1990, PNAS USA 87, 5968-5972). The DtxR protein, when complexed with $Fe^{2+}$, binds to the tox promoter and represses transcription of tox. Conversely, when iron is limiting, the un-complexed form of DtxR is unable to bind DNA, leading to induction of DT as a consequence of iron starvation. In addition to its role in DT production, DtxR is a global regulator of gene expression, regulating the expression of multiple genes involved in iron metabolism, protection against oxidative stress, and pathogenesis (Schmitt et al., 1997, Infect. Immun. 65, 5364-5367; Schmitt, 1997, Infect. Immun. 65, 4634-4641; Schmitt and Holmes, 1994, J. Bacteriol. 176, 1141-1149; Lee et al., 1997, Infect. Immun., 65, 4273-4280; Kunkle and Schmitt, 2003, J. Bacteriol. 185, 6826-6840). DtxR is also the prototype member of a large family of bacterial gene regulators found in numerous medically relevant bacterial species, and the proteins of this family share structural and functional similarities (Feese et al., 2001, In Messerschmidt et al. (eds) Handbook of Metalloproteins, John Wiley and Sons, Chichester, pp. 850-863).

Characterizing DtxR-dependent pathways at the molecular level is pivotal in understanding the (linked) phenomena of diphtheria pathogenesis, the mechanisms of iron-dependent gene expression, and responses to oxidative stress. However, until recently there was a distinct lack of tools for defined and targeted manipulation of chromosomal DNA in C. diphtheriae and other Coryneform bacteria. Early investigations of C. diphtheriae gene function relied on random chemical mutagenesis or the cloning of C. diphtheriae genes in E. coli. An additional technical challenge to overcome is that direct transformation of Corynebacterium species with DNA is significantly hampered by both the relatively impermeable Coryneform cell wall, as well as host DNA restriction barriers (Puech et al., 2001, Microbiol. 147, 1365-1382). Despite these drawbacks, some key results have recently extended the systems available for genetic manipulation of C. diphtheriae. First pNG2, a plasmid capable of replicating in C. diphtheriae has been isolated and characterized (Tauch et al., 2003, Plasmid 49, 63-74). Second, conjugal transfer of DNA from an E. coli donor to a C. diphtheriae recipient (followed by integration of the transferred DNA into the chromosome via homologous recombination) has been reported (Ton-That et al., 2004, Mol. Microbiol. 53, 251-261); providing an alternative to electroporation as a mechanism for introducing foreign DNA into the C. diphtheriae cytoplasm. Third, the homologous recombination pathway has also been exploited in a targeted allelic exchange method; where plasmids carrying a portion of a Corynebacterium gene, when transformed into C. diphtheriae or C. ulcerans, were capable of integrating into the chromosome (Schmitt and Drazek, 2001, J. Bacteriol. 183, 1476-1481). Fourth, use of the Tn5 transpososome system for mutagenesis resulted in isolation of the first marked mutations in C. diphtheriae; the first characterization of a dtxR null mutant, and the demonstration that DtxR is not essential for cell survival (Oram et al., 2002, J. Bacteriol. 184, 5723-5732). Following on from these advances, the recently determined genome sequence of a pathogenic C. diphtheriae clinical isolate, NCTC13129 (Cerfeno-Tarraga et al., 2003, Nucl. Acid Res. 31, 6516-6523) will aid further genetic studies of C. diphtheriae.

In other bacterial systems, the availability of a genome sequence has facilitated the development of vector systems for the targeted insertion of DNA. Such systems typically exploit the integrase protein and attP site of temperate bacteriophages, or prophages identified by genomics studies. When the vector is introduced into the host cytoplasm the phage integrase protein catalyses a site-specific recombination reaction between the vector-borne attP site and the chromosomal attB locus. This generates the recombinant attL and attR sites and causes integration of the vector (which can include virtually any foreign DNA sequence) into the chromosome. Some notable examples using this methodology include the stable transformation of Mycobacterium tuberculosis, Mycobacterium smegmatis and BCG strains using the tyrosine integrase proteins of φRv1 or L5 (Kee et al., 1991, PNAS USA 88, 3111-3115; Bibb and Hatfull, 2002, Mol. Microbiol. 45, 1515-1526). Additionally, the serine integrase protein from Streptomyces phage Φ31 has been used in the construction of an integration vector capable of integrating DNA into eukaryotic chromosomes, with great potential for use in gene therapy (Groth et al., 2000, PNAS USA 97, 5995-6000). Most relevant to the current work is the description of a vector utilizing the integrase protein and attP site from the C. glutamicum corynephage Φ16 (Moreau et al., 1999, Microbiol. 145, 439-548) that transformed C. glutamicum host strains. In addition, a strain of Arthrobacter aureus and other strains of C. glutamicum that are not normally permissive hosts for Φ16 could also be transformed with the same vector by virtue of the appropriate attB sequence being present in the chromosome of all the transformed species.

To facilitate the molecular characterization of gene regulatory pathways in C. diphtheriae, we developed a vector system that exploits the attP site and integrase protein of phage β. One attractive feature of using the β site-specific recombination system is that C. diphtheriae carries two closely-spaced attB sites designated attB1 and attB2 (Rappuoli and Ratti, 1984, J. Bacteriol. 158, 325-330), which allows for single β lysogens to serve as potential recipients for the integrating vector at the second uninterrupted attB site.

We further combined the β integrase functions with a conjugal transfer origin to facilitate delivery of DNA to the *C. diphtheriae* cytoplasm via conjugal mating with an *E. coli* donor. Delivery of the vector generated *C. diphtheriae* transformants at efficiencies equal or even superior to that obtained with a replicating *C. diphtheriae* plasmid. To further develop this system we used the newly constructed vector to restore the dtxR gene to a previously constructed ΔdtxR strain, with a consequent restoration of wild-type DtxR phenotypes. Finally, since both *C. glutamicum* and *C. ulcerans* species possess the β attB site(s) (Cianciotto et al., 1990, FEMS Microbiol. Lett. 66, 299-301), we demonstrated that these two species could also be transformed with the β phage-based vectors, thus establishing the utility of this vector system for species other than *C. diphtheriae.*

SUMMARY OF THE INVENTION

The present invention provides a system for site-specific directed gene insertion of desired genes or foreign DNA into cellular genomes. Using a bacteriophage-integrase technique, insertions of desired genes into a chromosome containing an attachment sequence recognized by the integrase can be achieved. The sites of insertion can be easily mapped. A site-specific integration vector has been designed which permits the study of promoter-operator regulation as well as allows complementation of inactivated genes at near wild-type levels of expression.

Therefore, in one aspect, the present invention provides novel vectors to integrate DNA into the genome of Gram-positive, Gram-negative, *Mycobacterium*, bacteria. In another aspect, the invention provides novel vectors to integrate DNA into the genome of *Corynebacteriae* for example, *C. diphtheriae, C. glutamicum* and *C. ulcerans.*

In yet another aspect, the present invention provides novel vectors for inserting mutations into *Corynebacteriae* or for complementing mutations in the *Corynebacteriae* genome. The vectors are useful for chromosomal manipulation of *Corynebacterium* species, for characterizing biochemical events giving rise to pathogenesis and other gene expression pathways in both medically and commercially relevant Coryneform species. In addition, these vectors can be used to express genes of interest from the chromosomes of any bacterial species resulting in stable over-production of a desired product. Two separate integrating plasmids can be used to create two differing and novel integrated sequences.

The vectors comprise a DNA fragment comprising (a) a polynucleotide encoding a functional integrase protein which can catalyze the site-specific recombination reaction; and (b) an attachment/integrase recognition site recognized by the integrase of (a).

Integration of the vector into the genome occurs at an attachment site in the chromosome of the host strain. Attachment sites can be inserted in a genome if one does not occur naturally.

The vectors for Gram positive bacterial hosts such as *C. diphtheriae* comprise a polynucleotide encoding an integrase from β phage or a β-like corynephage, for example the int gene from NCTC13129, and a recognition site recognized by the integrase, for example attP for use in transforming bacteria with a primary attachment site in its chromosome, for example attB.

In another aspect, the present invention provides a method for efficiently transforming *Corynebacteriae* with the plasmid of the present invention said method comprising mobilization of the desired plasmid from *E. coli* to *C. diphtheriae* by conjugation. In this case, a conjugal transfer origin is added to the vector to facilitate delivery via conjugal mating with a suitable donor, e.g. a mobilizing *E. coli* strain. No specific arrangement of the different elements on the vector is required. The transferred DNA is unable to replicate as an episome. The conjugation system is capable of transferring large plasmids (>10 kb) efficiently. Site-specific recombination mediated by integrase occurs between the transferred DNA and the *C. diphtheriae* chromosome results in insertion of the desired gene into the genome of *C. diphtheriae.*

In still another aspect, the present invention provides a transformant transformed by using the plasmid vector, a transgenic animal includes a chimeric animal other than humans, in which the plasmid vector has been integrated into the genome thereof.

In yet another aspect present invention provides a method for producing a useful substance, desired antigen, or vaccine. The method includes providing to a cell, the vector described above wherein the vector includes a desired DNA encoding the desired protein, antigen or vaccine, and a control region for controlling the expression of the protein, such as a promoter that functions in the host; introducing the vector into a host cell; and allowing the DNA segment to integrate into the genome of the host cell such that the protein encoded by the desired DNA segment is expressed in the host cell to produce the useful product. The cell wherein the product is expressed can be a bacterial cell, a vertebrate cell, or a mammalian cell, or a cell which is part of a transgenic animal.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

BRIEF DESCRIPTION OF THE DRAWINGS

FIG. 1. Maps of integration vectors. Relevant features in each vector are shown approximately to scale within each separate map (more details are given in the Materials and Methods). pKMO3W was assembled from the Bam HI-Sph I fragment of pK903, a Sph I-Pst I fragment carrying the β attP region and a Pst I-Bgl II fragment carrying the NCTC13129 DIP0182/int gene. A Kpn I fragment from pK18mobsacB, carrying the RP4 oriT was subsequently inserted into the Kpn I site of pKMO3W to yield pKMO3W+mob, and extraneous sequences between two Sac I sites was removed to give pK-AIM. A Sac I fragment carrying dtxR was added to form pK-AIMdtxR. In addition a novel polylinker, assembled by annealing two oligonucleotides, was added between the adjacent Eco RI and Sac I sites of pK-AIM to create pK-PIM FIG. 2. Site specific integration mediated by β-like corynephages. Shown as a dotted line is the episomal circular element (ie the phage or integrating plasmid vector) that includes attP (striped boxes) and int (black arrow). Additional genes may be included but are not essential. In the case of a toxigenic corynephage tox (white arrow) is present on the phage chromosome. The region of a (non-lysogen) *C. diphtheriae* host chromosome that includes attB1 and attB2 (grey boxes) is shown below the circular element. The DIP numbers are based on the annotation of strain NCTC13129. Chromosome maps of strains in which insertions occur at attB1, attB2 or both attachment sites are shown on the right. The attL and attR sites that result following site-specific integration mediated by Int between attP and attB are shown. Figure is not drawn to scale.

FIGS. 3A, 3B, 3C, 3D, 3E, 3F. Profiles of Strains in the PCR Screen. The presence or absence of the attB1 or attB2 sites was detected by PCR on recombinant clones, using oligos which hybridize in the immediately flanking open reading frames. The recombinant attL or attR sites were revealed by using the permutations of the bacterial- or phage-based oligo sequences given in Table 1. The PCR reactions were designed to detect the att site indicated above the lane. (A-C) the screen performed on the C7(−), C7(β) and NCTC13129 strains. (D-F) screens performed on isolates from C7(−) transformed with pKMO3W.

Figure 4:
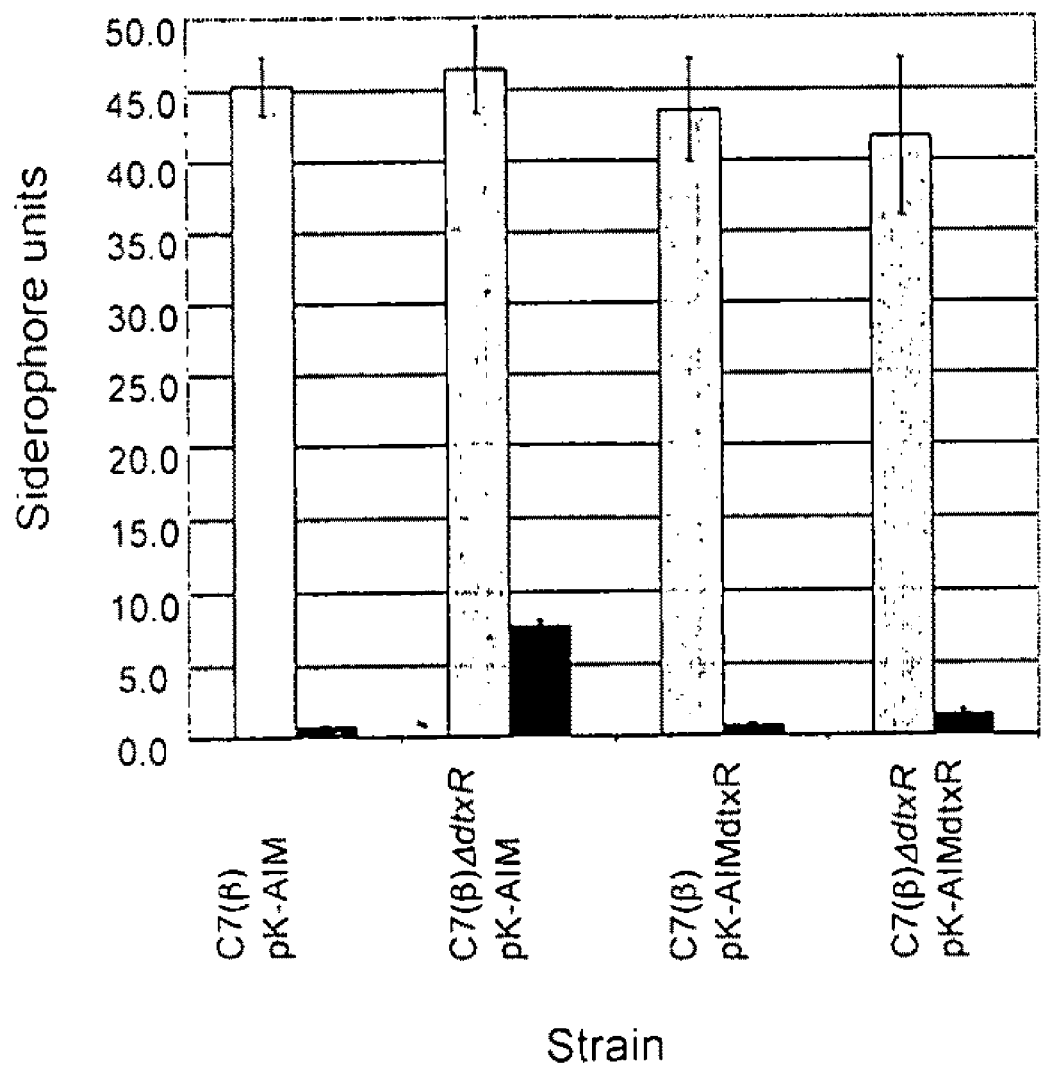

FIG. 4. Siderophore assays. Total siderophore units (the average of at least three experiments) produced by each strain during overnight growth in high (black bars) and low (grey bars) iron PGT medium. Error bars indicate the standard deviations.

DETAILED DESCRIPTION

As used herein, the term "introduction of a gene" refers to introduction of a gene into cells, and the term "integration of a gene" refers to incorporation of a gene into the genome of cells. However, when the term "introduction" is used in the context of transgenic animals, it means "integration."

Therefore, in one aspect, a DNA fragment able to integrate into a host genome is described. The DNA fragment comprises (a) an integrase gene; and
(b) a segment of DNA serving as an integrase recognition region or attachment site when integrase catalyzes the integration reaction.

Optionally, the DNA fragment can also include (c) any desired DNA segment to be integrated into the genome of host cells.

Thus, any desired DNA segment (c) can be inserted into the genome of a host cell by incorporating any DNA segment (c) of interest into the vector containing (a) through (b) using ordinary methods, and introducing the vector into the host cell.

A vector, as used herein, refers to a plasmid, a viral vector or a cosmid that can incorporate nucleic acid encoding the nucleic acid fragment of this invention. The term "coding sequence" or "open reading frame" refers to a region of nucleic acid that can be transcribed and/or translated into a polypeptide in vivo when placed under the control of the appropriate regulatory sequences.

The vector of the present invention can be prepared by incorporating the DNA components (a), (b), and optionally (c), into a plasmid. Plasmids into which these components are to be incorporated are selected based on factors such as the size of the DNA to be integrated into the genome of a host cell and the ease of handling. A known plasmid for which a restriction map has already been established may be used, for example those of pUC series, pBR series, and pACYC series. Any plasmid that fails to replicate as an episome in the cell-type of interest can be used to deliver the integrating vector. A replicating plasmid can also be used if both integration of the vector and episomal replication is desired.

The integrase gene, int, of the present invention is derived from corynephage β or a β-like phage and encodes an integrase useful in the present invention. A functional integrase includes any integrase, or portion of an integrase able to recognize the integrase-recognition sequence, cut the introduced vector, and integrate the cut DNA at the attachment site in another DNA is part of the present invention. In one embodiment of the present invention, the int gene is as specified in SEQ ID NO:1. All codons including the STOP codon and 200 bp upstream of the int gene has been found to be sufficient. As described below, some differences in integrase sequence are permissible as long as they have no major effect on integrase function.

The vector of the present invention may also contain a segment of DNA that serves as a recognition region recognized by integrase when integrase catalyzes the integration reaction (which may be referred to as an integrase recognition region or attachment site throughout this specification). The integrase recognition region contains at least a region which is recognized by integrase as its substrate when integrase catalyzes the integration reaction. In one aspect of the invention, the attP site is used or a portion thereof which is recognizable by the integrase. In one embodiment of the present invention, the attP site is 452 bp specified in SEQ ID NO:2.

The integrase attachment site is found in the target DNA, i.e. where the integration is targeted. The attachment site for the β phage or β-like phage integrase are known as attB sites, a sequence of less than 100 bp containing a sequence of about 90 bp, which shares identity with the attP site required for site-specific recombination crossover. Both attP and attB must contain a core region of about 90 bp for integrase to function. In one embodiment of the present invention, the attB site is specified in SEQ ID NO:3. attB-like sequences are found in many bacterial genera including *Tropheryma*, *Nocardia*, *Mycobacterium* and *Bacillus* among others. In some species, such as *Corynebacteriae*, two closely-spaced attB sites designated attB1 and attB2 are found. These sites allow for site-specific integration to occur at either site, leaving an open site for additional site-specific integration of another gene of sequence as desired. In addition, an attB site can be introduced into a genome that fails to contain a recognized site using standard molecular biology techniques for the organism of interest, i.e. standard cloning, PCR, and homologous recombination techniques known to a person with skill in the art, thereby facilitating use of these integration vectors in any genome.

Examples of host cells into which the plasmid vectors of the present invention are to be introduced include, but are not limited to, microorganisms such as *Mycobacterium*, Gram-positive bacteria, Gram-negative bacteria; yeast; cultured plant or animal cells; and cells in living plants or animals. Once introduced into host cells, the vectors of the present invention are efficiently integrated into the genome of host cells with the help of the components such as integrase gene in the vector. Accordingly, transformants transformed by the vectors of the present invention can be obtained.

The integrase facilitates integration of the nucleic acid fragment of this invention into both pluripotent (i.e., a cell whose descendants can differentiate into several restricted cell types, such as hematopoietic stem cells or other stem cells) and totipotent cells (i.e., a cell whose descendants can become any cell type in an organism, e.g., embryonic stem cells). It is likely that the gene transfer system of this invention can be used in a variety of cells including animal cells, bacteria, fungi (e.g., yeast) or plants. Animal cells can be vertebrate or invertebrate. Cells such as oocytes, eggs, and one or more cells of an embryo are also considered in this invention. Mature cells from a variety of organs or tissues can be targeted. Cells receiving the nucleic acid fragment include, but are not limited to, lymphocytes, hepatocytes, neural cells, muscle cells, a variety of blood cells, and a variety of cells of an organism. Methods for determining whether a particular cell is amenable to gene transfer using this invention include searching the genome sequence for polynucleotide sequences that are similar to the attB sequence and transforming the cell with the vector to test for insertion. The cells can be obtained from vertebrates or invertebrates.

Vertebrate cells can also incorporate the nucleic acid fragment of this invention. Cells from fish, birds and other animals can be used, as can cells from mammals including, but not limited to, rodents, such as rats or mice, ungulates, such as cows or goats, sheep, swine or cells from a human.

The DNA of a cell that acts as a recipient of the nucleic acid fragment of this invention includes any DNA in contact with the nucleic acid fragment of this invention. For example, the DNA can be part of the cell genome or it can be extrachromosomal, such as an episome, a plasmid, a circular or linear DNA fragment. Targets for integration are double-stranded DNA.

In one aspect of this method, the introducing step comprises a method for introducing nucleic acid into a cell selected from the group consisting of: electroporation, transfection, conjugation, microinjection; combining the nucleic acid fragment with cationic lipid vesicles or DNA condensing reagents; and incorporating the nucleic acid fragment into a viral vector and contacting the viral vector with the cell. Preferred viral vectors include, but are not limited to, the group consisting of a retroviral vector, an adenovirus vector or an adeno-associated viral vector.

This invention also relates to transgenic animals produced by this method. Where transgenic animals are produced, the nucleic acid fragment may comprise segment (a) and (b) further and further contain a sequence (c) which preferably encodes a protein and preferably a protein to be collected from the transgenic animal or a marker protein. The invention also relates to those cells of the transgenic animal expressing the protein encoded by the nucleic acid sequence.

For production of a desired antigen or vaccine, a vector is prepared by inserting, the DNA segment (c), a segment of DNA encoding a useful protein or vaccine antigen, as well as an expression control region such as a promoter for allowing the expression of the DNA, into a vector containing the components (a) and (b). Promoters include constitutive promoters and inducible promoters. The vector is introduced into host cells to integrate the DNA segment (c) into the genome of the host cell. The useful protein encoded by the DNA is then expressed as desired.

When somatic cells of living animals are used as the host cells, somatic chimeras or transgenic animals can be produced and used to produce the desired substances. For example, useful substances may be produced in milk of mammals including cows, goats, sheeps, and hogs, or in eggs of birds including chickens, ostriches, and ducks.

When bacterial cells are used, large quantities of the desired product can be produced and easily purified from fermentor cultures or the like. Stable expression of the desired product from a site in the genome provides an advantage over traditional expression from an episomal vector. Episomal vectors are less stable and must be maintained with selection while insertion of a vector in the genome does not require continued selection.

The DNA fragment of the present invention having the components (a), (b), and the DNA segment (c) encoding an antigen capable of producing a protective immune response against an infection in a subject may be used as DNA vaccines. In order to serve as a DNA vaccine, the vector is constructed such that it contains a segment of DNA encoding a protein that acts as an antigen in cells of the animals of interest, as well as a DNA segment joined with the segment such as promoter for facilitating and/or controlling the expression of the protein. For example, DNA segment encoding protective antigens of infectious diseases of human or non-human vertebrates, may be used.

The vectors which are the DNA vaccines are prepared in various forms generally used in application of vaccines including liquid formulations, injections, dry formulations, capsules, gold colloids, powder sand particulates and the like. Preferably, the vectors are prepared in the forms of liquid formulations for oral administration, dry formulations for oral administration, capsules, particulates and injection, and particularly, in the forms of dry formulations for oral administration.

Preferred methods for administering the DNA vaccine include injection and oral administration. In case of injection, the vaccine prepared in the form of injection may be injected into the body of subjects according to ordinary methods. It has been reported that antibodies in blood and secretory IgA were induced by orally administering particulated plasmid DNA (Jones, D. H., et al., Vaccine, 15, 814-817, 1997). The vectors of the present invention may be orally administered according to the methods such as those described in this article. Advantages of orally administering DNA vaccines include readiness of administration and reduction in side effects such as inoculation reactions at the site of administration. In addition, oral administration of DNA vaccines is particularly advantageous in that local immunity can be induced, preventing infection of many pathogens that enter from mucosal surface.

The induction of immune responses by the use of plasmids requires large quantities of DNA, thus DNA vaccines have not been put to practical use hitherto. One reason for this is that, once introduced into cells, the plasmid DNA is eliminated in a short period of time. In contrast, the vaccines using the vectors of the present invention make it possible for the plasmids introduced into cells to integrate into the genome of the cell such that the antigens are continuously produced. Accordingly, the vaccines using the vectors of the present invention have the ability to induce strong immune responses by providing strong stimulation to immune systems without requiring large quantities of DNA as in the conventional approaches.

The DNA of a cell that acts as a recipient of the nucleic acid fragment of this invention includes any DNA in contact with the nucleic acid fragment of this invention in the presence of an integrase. For example, the DNA can be part of the cell genome or it can be extrachromosomal, such as an episome, a plasmid, a circular or linear DNA fragment. Targets for integration are double-stranded DNA.

The present invention additionally provides kits comprising the integrating vectors of the present invention, along with appropriate buffers, diluents, vessels and/or devices, etc. for integrating a gene of interest into a cell, for example, for overexpressing a gene of interest from a chromosomal location. The kit may contain any of the vectors described in this application, i.e. having a DNA fragment comprising an integrase and an integrase-recognition sequence, in addition to other genes necessary for detection of the transformed cell, or other sequences necessary for insertion of the desired genes.

The present kits comprise a first container means containing one or more of the above-described vectors. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

All publications, including, but not limited to patents and patent applications, cited in this specification are herein incorporated by reference as if each individual publication were specifically and individually indicated to be incorporated by reference herein as though fully set forth.

The invention is further described in detail to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided therein.

The following Materials and Methods were used in the Examples below.

Materials and Methods

Cultivation Conditions and Media

*C. diphtheriae* and *C. ulcerans* were grown in heart infusion broth (Difco) supplemented with 0.2% Tween 80 at 37° C. with agitation. *C. glutamicum* was grown in Luria-Bertani (LB) broth (Sambrook and Russel, 2001 Molecular Cloning A Laboratory Manual. Third ed. Cold Spring Harbor Laboratory Press, Cold Spring Harbor, N.Y.) at 37° C. with agitation. *E. coli* strains DH5α (Bethesda Research Laboratories, Gaithersburg, Md.) and TE1 (Jobling and Holmes, 2000, PNAS USA 97, 14662-14667) were used as hosts for cloning and were regularly cultivated at 37° C. with agitation in LB broth. Antibiotics were used at the following concentrations: for *E. coli* kanamycin at 25 μg per ml, for *Corynebacterium* kanamycin at 10 μg per ml and nalidixic acid at 20 μg per ml.

Transformation of *Corynebacterium* Species

Electroporation was used to introduce DNA into *C. diphtheriae* (Oram et al., 2002, supra). The plasmid pKN2.6 (Schmitt and Holmes, 1991, supra) which confers resistance to kanamycin and contains an origin of replication that functions in *C. diphtheriae* was used as a positive control for electroporation. Matings were performed using *E. coli* S17-1 containing an RP4 mobilizable plasmid as the donor and strains of *C. diphtheriae, C. glutamicum* or *C. ulcerans* as the recipients. In all cases matings were performed essentially as previously described (Oram et al., 2006, J. Bacteriol. 188, 2959-2973) using resistance to nalidixic acid to select for the Coryneform species.

Construction of Integrating Vectors

Restriction enzymes and other DNA modification enzymes from various commercial suppliers were obtained through the BIORESCO freezer program of the University of Maryland. All enzymes were used according to the manufacturer's instructions, and standard cloning procedures were followed throughout (Sambrook and Russel, 2001, supra). PCR reactions were performed with Taq polymerase (Fermentas Life Sciences), and restriction-digested PCR fragments or plasmids were purified from agarose gels with the UltraClean kit (Mo Bio Laboratories). The correct assembly of each construct was verified by restriction mapping and DNA sequencing.

FIG. 1 shows the maps of the integrating vectors constructed in this work. The plasmid pK903 is a pUC19 (Yanisch-Perron et al., 1985, Gene 33, 103-119) derivative that confers kanamycin resistance, constructed by ligating 1748 bp SspI to DraI fragment of pUC19 and a 930 bp fragment of EZ-Tn5<KAN-2> (Epicentre) containing the aph gene. pK903 was the parental plasmid of the vectors constructed here. First, pKMO3W was assembled from the following DNA fragments. The DIP0182/int gene was obtained by PCR using NCTC13129 genomic DNA as a substrate; with primers ϕ-INT-PstI (5' GTG TAA AGT GGG CTG CAG CTA ACC (SEQ ID NO:4): equivalent to nt 155,582-155,605 of the annotated genome sequence) and ϕ-INT-BglII (5' CGT GAG ATC TCT GCA TAA GCA ATA G (SEQ ID NO:5): the reverse complement of nt 156,926-156,950). The attP site was generated by PCR using corynephage β DNA as a substrate, with primers ATTP-UP-SphI (5' AGG TGC ATG CTA AGC TAT CGC TAT TTT TTG AAA (SEQ ID NO:6)) and ATTP-DN-PstI (5' TTC TAA CTG CAG GTC AGC TGT GTC GAG TTC (SEQ ID NO:7)). The SphI/BamHI-cut pK903, BglII/PstI-cut DIP0182/int DNA and PstI/SphI-cut attP DNA fragments were mixed and ligated together to yield pKMO3W (4425 bp (SEQ ID NO:8)). The oriT transfer DNA origin was obtained from the 2.42 kb KpnI fragment of pK18mobsacB (Schafer et al., 1994, Appl. Environ. Microbiol. 60, 756-759): this was ligated into KpnI-cut and phosphatase-treated pKMO3W to yield pKMO3W+mob (6845 bp (SEQ ID NO:9)). pKMO3W+mob was then reduced in size by digesting with SacI: the largest 5.09 kb fragment was gel-purified and re-circularized with ligase to yield pK-AIM (5092 bp (SEQ ID NO:10). To make pK-AIMdtxR (6036 bp), a copy of the dtxR gene was inserted into the remaining SacI site of pK-AIM by ligation. This gene was obtained from a PCR reaction on NCTC13129 DNA with oligos dtxR-SacI-UP (5' GCC GAA AAA CTT GAG CTC TAC GCA CAA TAA AGC G (SEQ ID NO:11)) and dtxR-SacI-DN (5' CAT CTA ATT TCG AGC TCT TTA ATA TTT AGA G (SEQ ID NO:12)). This insert can be present in one of two possible orientations in pK-AIM: we selected and subsequently used a clone where the dtxR gene was transcribed in the same direction as the int gene of pK-AIMdtxR. To construct pK-PIM, pK-AIM was first partially digested with EcoRI, and then with SacI. A fragment 5090 bp in size was gel-purified and used for ligation with a linker fragment. This was obtained from oligos polylinker1 (5' CTT AAT TAA CGT TAA CTA GTA GAT CTG GGC CCC GCG GCG GCC GCA CGT G (SEQ ID NO:13)) and polylinker2 (5' AAT TCA CGT GCG GCC GCC GCG GGG CCC AGA TCT ACT AGT TAA CGT TAA TTA AGA GCT (SEQ ID NO:14)), which were annealed together by mixing equimolar (40 μM) amounts in 1X NEB#2 (New England Biolabs), heating to 85° C. for 5 min and then allowed to cool slowly to room temperature. The linker DNA fragment thus obtained was ligated with SacI/partial EcoRI-cut pK-AIM to yield pK-PIM (5139 bp, SEQ ID NO:15).

Detection of Integrants

Kanamycin-resistant colonies obtained from transformation of *C. diphtheriae* strains with an integrating vector were screened for insertion events at attB1 or attB2 by PCR. A sample of each colony was re-suspended in 35 ul water and heated at 95° C. for 5 min: the cellular debris was then pelleted by centrifugation at 5,000×g for 5 min. Six 5 ul aliquots of the supernatants were used in six separate PCR reactions. The primers used were ATTP-UP (5' AGG TGC ATG CTA AGC TAT CGC TAT TTT TTG AAA (SEQ ID NO:16); ATTP-DN (5' TTC TAA CTG CAG GTC AGC TGT GTC GAG TTC (SEQ ID NO:17); ATTB1-UP (5' GGC TCA ATC TGA TCG GCG TGG TGC T (SEQ ID NO:18)); ATTB1-DN (5' GGC GAG TAG GCA CGC AGC AAG AAA AA (SEQ ID NO:19)); ATTB2-UP (5' CGT ACG TCG GGA TCT GGG AAA GGT GGT CT (SEQ ID NO:20)), and ATTB2-DN (5' CGA AGA CTC TAG TGT AAT CGG TGT A (SEQ ID NO:21)). The combinations of these primers used to detect each att site are listed in Table 1. PCR reactions were performed with a cycle profile of 94° C., 30 sec; 55° C., 30 sec; 72° C., 60 sec (22 cycles) and reactions were resolved directly on 1% agarose gels. Integration events in *C. glutamicum* attB1 or attB2 sites were detected as above with oligos ATTP-UP; ATTP-DN; ATTB1g-UP (5' CTG AAC ATC ATC GCA GTC ATC CTC ATT ACG (SEQ ID NO:22); ATTB1g-DN (5' CGG CGC ACG GAT CGA AGT GTT C (SEQ ID NO:23)), attB2g-UP (5' CAT AAG TAG GGA TAG TTG CCA AAT CTG CTC (SEQ ID NO:24) or ATTB2g-DN (5' TGT CGA GAA ACG AAT GCC CCA GTT TCA CCC (SEQ ID NO:25). Integration of vector DNA at *C. ulcerans* attB sites was detected using oligos ATTBu-UP (5' CCA CCT ATG CGC CCG TAG CTC (SEQ ID NO:26) and ATTBu-DN (5' CAA CAA TCC ACC AAC CAA ACA CAC (SEQ ID NO:27)).

Siderophore Assays

Siderophore assays were performed as described previously (Oram et al., 2002, supra). A standard curve was constructed by performing assays with ethylenediamine-N,N'-diacetic acid (EDDA) at concentrations from 50 µM to 1 mM. One siderophore unit was defined as the $A_{630}$ of a control assay performed with a 0.5-ml sample of 1 mM EDDA.

TABLE 1

| Site detected | Primer pair | Predicted size (bp) |
|---|---|---|
| attP | ATTP-UP & ATTP-DN | 409 |
| attB1 | ATTB1-UP & ATTB1-DN | 736 |
| attB2 | ATTB2-UP & ATTB2-DN | 831 |
| attL1 | ATTB1-UP & ATTP-DN | 475 |
| attR1 | ATTP-UP & ATTB1-DN | 670 |
| attL2 | ATTB2-UP & ATTP-DN | 599 |
| attR2 | ATTP-UP & ATTB2-DN | 641 |
| Cg attB1 | ATTB1g-UP & ATTB1g-DN | 464 |
| Cg attB2 | ATTB2g-UP & ATTB2g-DN | 718 |
| Cg attL1 | ATTB1g-UP & ATTP-DN | 511 |
| Cg attR1 | ATTP-UP & ATTB1g-DN | 353 |
| Cg attL2 | ATTB2g-UP & ATTP-DN | 591 |
| Cg attR2 | ATTP-UP & ATTB2g-DN | 527 |
| Cu attB1 | ATTBu-UP & ATTBu-DN | 150 |
| Cu attB2 | ATTBu-UP & ? | n/d |
| Cu attL1 | ATTBu-UP & ATTP-DN | 329 |
| Cu attR1 | ATTP-UP & ATTBu-DN | 243 |
| Cu attL2 | ATTBu-UP & ATTP-DN | (330) |
| Cu attR2 | ATTP-UP & ? | n/d | n/d = not determined and not detected. Size in parenthesize was the size detected; it could not be predicted because the sequence of Cu attB2 is not known.

EXAMPLE 1

Corynephage β Integration Functions and Construction of pKMO3W

The two attB sites for phage β (and closely related phages) in the *C. diphtheriae* chromosome are each partly contained within a duplicated tRNA$^{ARG}$ gene (anticodon ACG) (Ratti et al., 1997, Mol. Microbiol. 25, 1179-1181); a property shared with many other integrating phage systems (Campbell, 1992, J. Bacteriol. 174, 7495-7499). The sites, which are named attB1 and attB2, flank gene DIP0179 (with the numbering based on the genome annotation of *C. diphtheriae* strain NCTC13129 (Cerdeno-Tarraga et al, 2003, supra)) such that the genetic loci in this region map in the order DIP0178-attB2-DIP0179-attB1. The acquisition of the tox gene (DIP0222) responsible for the toxigenic nature of NCTC13129 likely occurred as a result of integration of a β-like phage at the attB1 site in a progenitor strain, with the concomitant formation of the attL1 and attR1 sites flanking the prophage sequence.

We sequenced a region of corynephage β resident in strain C7(β) (Bardsdale and Papenheimer, 1954, J. Bacteriol. 67, 220-232) that includes the int gene, while the int gene (DIP0182) of the β-family phage in strain NCTC13129 was available from the annotated genome. Each gene encodes a tyrosine recombinase protein 408 amino acids in length, with 11 (highly conservative) amino acid differences over their total lengths. Perhaps most interestingly, in each of these two proteins, the histidine of the 'inviolate' RHR signature triad of the lambda integrase family (Argos et al., 1986. EMBO 5. 433-440) is replaced with a tyrosine residue. This histidine to tyrosine substitution in a lambda-like recombinase is rare but not undocumented (Esposito and Scocca, 1997, Nucl. Acids Res. 25, 3605-3614; Nunes-Duby et al., 1998, Nucl. Acids Res. 26, 391-406). None of the 11 differences between the two proteins alter residues that are highly conserved across other lambda integrase members. The respective attB and attP regions from NCTC13129 and β share a 92 bp common 'core' region (Cianciotto et al., 1986, J. Bacteriol. 168, 103-108): a region somewhat large compared with equivalent systems from other integrating bacteriophages. The entire β attP site, by analogy with other attP sites (Smith-Mungo et al., 1994, J. Biol. Chem. 269, 20798-20805; Pena et al, 1997, J. Mol. Biol. 266, 76092), likely extends beyond this core region, and the functional limits of the β attP site remain to be determined experimentally. The sequence conservation is exact over the first 50 bp between attP and attB1, or the first 54 bp between attP and attB2. The 3' half of each attB site, however, varies somewhat compared with the 3' half of attP (Cianciotto et al., 1986, supra).

Strain NCTC13129 provided a source of DNA in this work for PCR-generation of the attP site and int genes from the β-like phage resident in this isolate. The equivalent sequences from β itself were obtained from strain C7(β) DNA: in addition the progenitor strain C7(-) (Freeman, 1951, J. Bacterioil. 61, 675-688) was used as a recipient for some of the vectors constructed here. The first construct which we used extensively was termed pKMO3W (see FIG. 1 for plasmid maps and Materials and Methods for further descriptions of plasmid constructions). This vector and subsequent derivatives carried the entire DIP0182/int gene from NCTC13129 along with 200 bp upstream of the open reading frame to include the presumptive promoter. The pKMO3W vector also contained a 452 bp fragment of the β attP region, which included the 92 bp core along with 115 bp of the upstream and 245 bp of the downstream regions. A gene encoding resistance to kanamycin was included on the vector to enable selection of transformants, as well the colE1-derived replication origin from pUC19, which permits episomal propagation in *E. coli* but not *C. diphtheriae*. The absence of a replication origin capable of functioning in *C. diphtheriae* ensured that kanamycin-resistant *C. diphtheriae* isolates formed after transformation with this construct would be indicative of a recombination event between the vector and chromosome resulting in integration.

EXAMPLE 2

Electroporation of pKMO3W into *C. diphtheriae*

Figure 2:
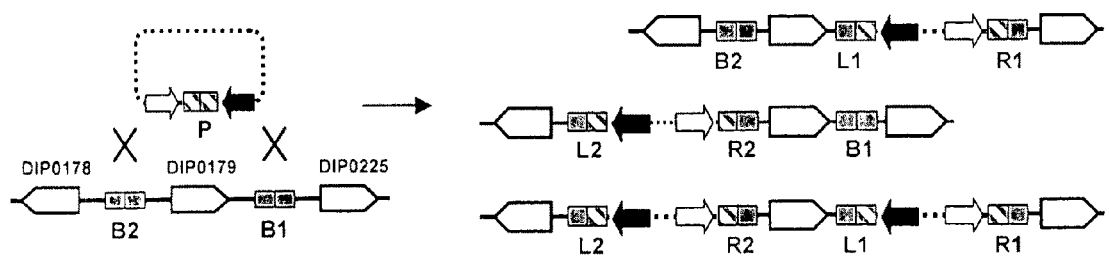
Figure 3:
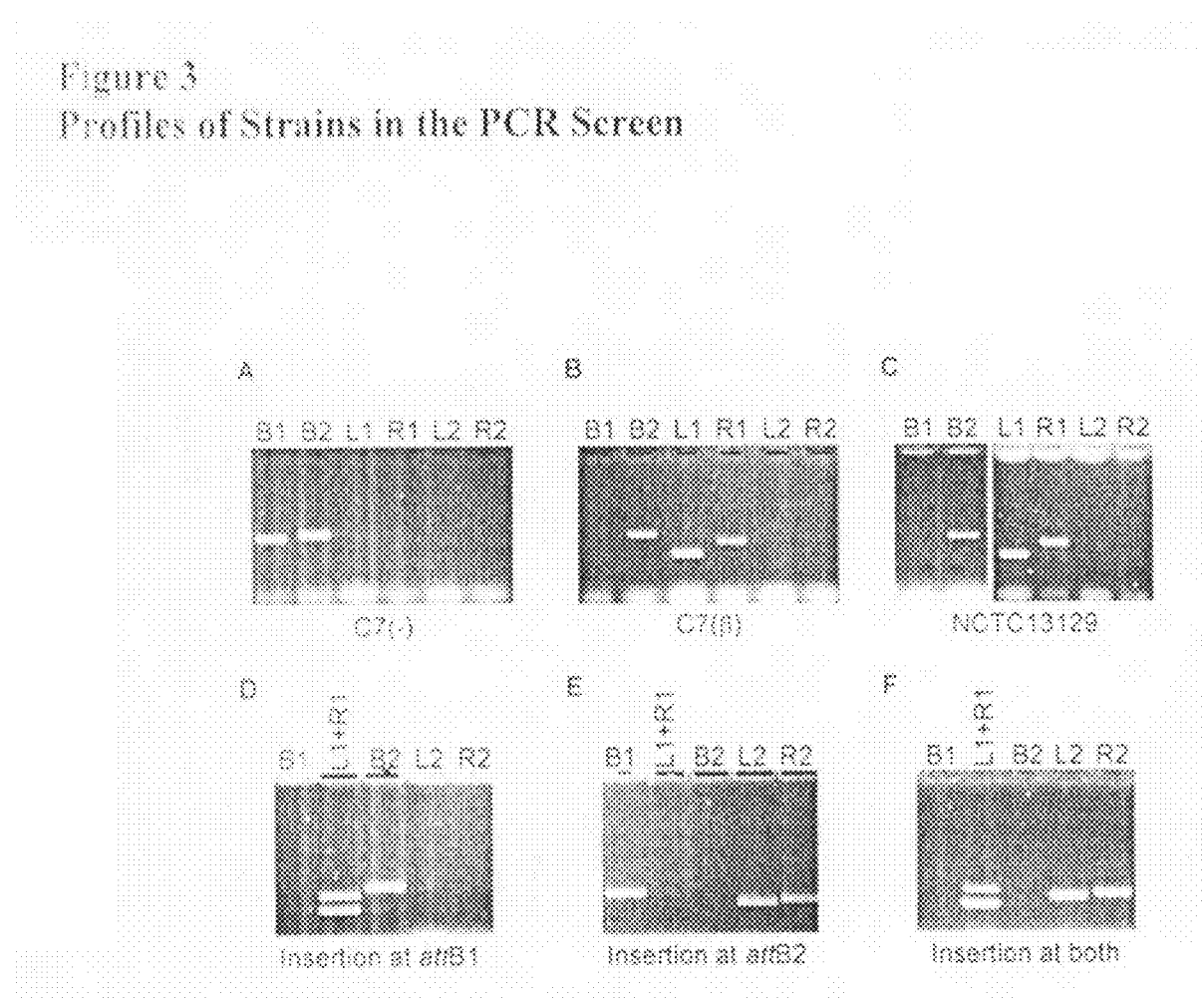

We first attempted to deliver pKMO3W to the cytoplasm of C7(-), C7(β) or NCTC13129 by electroporation. The efficiency of transformation was very low (<1 transformant per μg DNA), although a clear increase of approximately 5-fold was observed when using DNA that had been previously passaged through a dam dcm *E. coli* host prior to electroporation. In addition, the numbers of transformants recovered from electroporation of C7(−) with pKMO3W increased when increasing quantities of unmethylated input DNA were used (data not shown).

Integration events at the attB1 or attB2 sites in these strains were detected with a PCR-based screening approach. The basis of this screen was that convergent oligo primers designed to hybridize in the open reading frames immediately flanking the attB1, attB2 or attP sites (FIG. 2) would yield products, but only while these sites remained intact. An integration event leading to the destruction of attB would then produce a strain which no longer gave a positive signal in a PCR reaction when the corresponding flanking primers were used. Instead, suitable permutations of oligos (Table 1) could be used to reveal the formation of the recombinant attL and attR sites. The DNA of transformant colonies was screened in six PCR reactions performed in parallel: each with a differing combination of upstream and downstream oligos, designed to reveal the presence or the absence of the attB1, attL1, attR1, attB2, attL2 or attR2 sites. As an example, the PCR profiles of the three host strains using this assay are shown in FIGS. 3A-3C. The C7(−) host had both attB1 and attB2 sites intact, while both the C7(β) and NCTC13129 strains possessed attL1 and attR1 in place of attB1. This was as expected, since the respective β or the β-like phages have been previously mapped to the attB1 site in both cases (Cerdeno-Tarraga et al., 2003, supra; Rappuoli et al., 1983, J. Bacteriol. 153, 1202-1210)

Colonies arising from electroporation of C7(−) with pKMO3W were screened in exactly the same way, and some illustrative examples are also shown in FIGS. 3D and 3E. One experiment in which 40 ug of pKMO3W DNA was electorporated into C7(−) gave two colonies on kanamycin plates: one of these showed evidence of an integration event at attB1 (FIG. 3D) while the incoming DNA in the other isolate had recombined at attB2 (FIG. 3E). This result in itself established that the vector was capable of integrating into either attB site. In a separate experiment using 100 μgs of the same DNA to transform C7(−), 23 colonies were obtained: of these 12 had recombination occurring at attB1, and the remaining 11 had recombination at attB2. This latter result strongly implies the vector shows no preference in inserting into either attB site. Additionally we used electroporation to deliver pKMO3W to the cytoplasm of C7(β) and NCTC13129. In all of the resulting kanamycin-resistant transformants insertion of pKMO3W had occurred at the unoccupied attB2 sites.

EXAMPLE 3

Mobilization of Integrating Vectors from *E. coli* to *C. diphtheriae*

To provide an alternative method to electroporation for delivery of an integrating vector to *C. diphtheriae*, we next inserted an RP4 transfer origin oriT into pKMO3W. we termed the resulting vector pKMO3W+mob. *E. coli* S17-1 is an RP4 mobilizing host and can be used as the donor strain in matings with a *C. diphtheriae* recipient (Oram et al., 2006, supra). Mating reactions were set up with S17-1/pKMO3W+mob as the donor and C7(−) as the recipient. Kanamycin-resistant colonies were obtained in this manner, at a frequency comparable to that of the replicating plasmid, pCB303 (Table 2). [The plasmid pCB303 was constructed by inserting the 2.6 kb pCM2.6 EcoRI/ClaI fragment (ClaI end made blunt with T4 polymerase) that includes the pNG2 *C. diphtheriae* origin of replication (Schmitt and Holmes, 1991, supra) into pK19mobsacB digested with EcoRI and SmaI. The plasmid pK19mobsacB contains the RP4 origin of transfer (Schafer et al., 1994, supra).] Significantly more colonies were obtained with this method compared with the delivery by electroporation, and once again the PCR screen showed that integration had occurred in either of the attB1 or attB2 sites at near identical frequencies (data not shown). In addition we observed some rarer double integration events where insertions of pKMO3W+mob occurred both at attB1 and attB2 in the same cell (FIG. 3F).

TABLE 2

| Donor plasmid phenotype | Recipient | Mating frequency* |
|---|---|---|
| Replicating | *C. diphtheriae* | $8.0 \times 10^{-6}$ |
| Integrative | *C. diphtheriae* | $5.1 \times 10^{-6}$ |
| Replicating | *C. glutamicum* | $3.3 \times 10^{-9}$ |
| Integrative | *C. glutamicum* | $1.2 \times 10^{-9}$ |
| Replicating | *C. ulcerans* | $8.2 \times 10^{-5}$ |
| Integrative | *C. ulcerans* | $1.2 \times 10^{-4}$ |

*Number of transconjugants divided by number of donors

EXAMPLE 4

Confirmation that Integration Occurs Exclusively at the attB Sites

To demonstrate that insertions of pKMO3W or pKMO3W+mob occurred only at the attB sites and not at other locations in the chromosome of *C. diphtheriae* we performed Southern blots using a probe identical to a 1.2 kb region of both plasmids and that included the kanamycin gene. Following hybridization and detection, the blots were stripped and re-probed with labeled DNA identical to DIP0179: the region between attB1 and attB2 in the *C. diphtheriae* chromosome (FIG. 2). In strains in which insertions at both attB1 and attB2 were detected by PCR (FIG. 3F), two and only two insertion sites were identified in the Southern blot analysis with the kanamycin probe. In addition the bands containing these two sites also hybridized to the probe specific for the DIP0179/inter-attB site region. Similar results were obtained when DNA was isolated from a strain in which a single insertion had occurred either at attB1 or attB2; i.e., the Southern analysis detected only one band that hybridized both with the kanamycin probe and the attB-specific probe. We surveyed the chromosomal DNA of 20 different transformants isolated from 6 different transformations, and in all cases insertions were detected only at attB1 and/or attB2 (data not shown). Based on these results we infer that insertion of pKMO3W and its derivatives occurs solely at the attB sites.

EXAMPLE 5

Utility and Further Development of the Integrating Vector System

The above analyses using pKMO3W and pKMO3W+mob established the integrating vector as an efficient means to create targeted DNA insertions in *C. diphtheriae* in single copy. Following on from this, two other main vector derivatives were constructed. Firstly we deleted sequences from pKMO3W+mob which were not necessary for its function as a mobilizable integration vector (and which contained extraneous copies of otherwise useful restriction sites) to create pK-AIM (FIG. 1). We then added to pK-AIM a short region of DNA containing recognition sites for several novel restriction enzymes, to construct pK-PIM (FIG. 1). The presence of the polylinker in pK-PIM expands the versatility of the plasmid integration vector for insertion of novel DNA sequences that encode genes of interest. These plasmids were constructed to improve the utility of the system; and two further experimental approaches to this end, namely the complementation of a single gene deletion in C. diphtheriae, and the use of the vector in other species of Corynebacterium, are described below.

EXAMPLE 6

Complementation of an Inactivated C. diphtheriae Gene in Single Copy

The dtxR gene in C. diphtheriae is non-essential, since a C7(β)ΔdtxR deletion strain is viable. Nevertheless, the ΔdtxR mutant has a growth defect compared with C7(β) in high iron medium and is unable to regulate sideophore production in response to iron availability (Oram et al., 2006, supra). We thus determined if dtxR expressed from a novel chromosomal location (namely attB2) could complement the DtxR-dependent mutant phenotypes of C7(β)ΔdtxR. A copy of the wild-type dtxR gene was inserted into pK-AIM to create pK-AIMdtxR, and both C7(β)ΔdtxR and C7(β) were transformed with either pK-AIM or pK-AIMdtxR. A Southern blot analysis was used to confirm that the strain C7(β)ΔdtxR::pK-AIM-dtxR thus created carried a single copy of the full-length dtxR at the attB2 locus and a deleted copy ΔdtxR (not shown).

We performed the growth rate determinations in triplicate, and to standardize the rates we determined the doubling time of C7(β) during log-phase growth during each experiment and set this value to 1. Using this method the doubling times of the test strains in low iron medium were as follows: C7(β)::pK-AIM=1.0, C7(β)::pK-AIMdtxR=1.0, C7(β)ΔdtxR=1.2, C7(β)ΔdtxR::pK-AIM=1.2 and C7(β)ΔdtxR::pK-AIM-dtxR=0.98. In high iron medium the doubling times of all strains expressing a wild-type copy of dtxR decreased by approximately 3 to 5 minutes indicating an increased rate of growth. In stark contrast the doubling times of C7(β)ΔdtxR and C7(β)ΔdtxR::pK-AIM increased by approximately 3 to 5 minutes. These data indicate that the presence of the pK-AIM integration vector alone has no effect on the growth rate of *C. diphtheriae* and that expression of dtxR from pK-AIMdtxR inserted at attB2 is capable of restoring a wild-type growth rate to C7(β)ΔdtxR in both high and low iron media.

We also assayed the ability of each strain to regulate production of siderophore in response to iron in the growth medium. The results of this assay are shown in FIG. 4. C7(β)::pK-AIM was capable of suppressing production of siderophore in the presence of 10 μM $FeCl_3$ by approximately 50-fold. C7(β)ΔdtxR::pK-AIM suppressed production of siderophore in the presence of $FeCl_3$ by approximately 6-fold but it produced approximately 10 times more siderophore under high-iron conditions than strains that expressed dtxR. This result is equivalent to that observed previously with C7(β)ΔdtxR (Oram et al., 2006, supra). In contrast when pK-AIMdtxR was integrated into attB2 in C7(β)ΔdtxR, the ability to repress siderophore production by approximately 50-fold in the presence of $FeCl_3$ was restored. Thus a single copy of pK-AIMdtxR inserted at attB2 is sufficient to correct the defects of C7(β)ΔdtxR mutant in both the growth rate and the regulation of siderophore production in the presence of iron.

EXAMPLE 7

Use of the Integration Vectors in Other Species of *Corynebacterium*

The β attB site of *C. diphtheriae* is found in other Coryneform species (Cianciotto et al., 1986, supra), opening up the possibility that the techniques and vectors developed here could be used to transform other species of *Corynebacterium*. To test this hypothesis we focused on two species: *C. glutamicum* and *C. ulcerans*. *C. glutamicum* strains, while possessing two phage β attB sites (Cianciotto et al., 1990, supra), have not been shown to be susceptible to infection by β-like corynephages. *C. ulcerans* strains, by contrast, are permissive hosts for β-like phages; and strains possessing either one or two attB-hybridizing sequences have been detected by Southern blots (Groman et al., 1984, Infect. Immun. 45, 511-517). For these experiments, we used *C. glutamicum* ATCC 13032, a strain for which the genome sequence has been determined (Kalinowski, et al., 2003, J. Biotechnol. 104, 5-25), or *C. ulcerans* 712. This latter strain was chosen since it does not host a β-like phage and instead possesses two intact attB sites (Groman et al., 1984, supra). We used *E. coli* S17-1 as a donor to mate pKMO3W+mob or pK-AIM into each of these hosts. In all cases the frequency of transformation with the integrating vector was equal or better than that observed when a replicating plasmid (pCB303) was transferred using the same method (Table 2, below).

To confirm the presence of the integrating vector in the chromosome of the transformants we again utilized a PCR based method in each case. We designed novel oligo primers based on the *C. glutamicum* ATCC 13032 genome sequence, whose binding sites lie in open reading frames adjacent to the attB1 and attB2 sites, and used these primers in combination with the original attP-specific primers to detect insertions (Table 1). (Note that to maintain the convention used in *C. diphtheriae* the attB2 site in *C. glutamicum* is the first site encountered on the chromosome between Cgl0218 and Cgl0219 while attB1 lies between Cgl0225 and Cgl0226, following the gene annotation established in (Kalinowski et al, 2003, supra)). The intact attB1 and attB2 sites were readily detectable in the recipient strain prior to transformation and we detected insertions in either attB1 or attB2 in all kanamycin-resistant *C. glutamicum* transformants (data not shown). For example in strains in which attB1 was not detected we detected the presence of attL1 and attR1: similarly consistent results were obtained with strains in which the insertion occurred at attB2. This shows that pKMO3W (or derivatives) can integrate into either of the two attB sites present in the *C. glutamicum* chromosome.

For *C. ulcerans* 712, formation of lysogens with the phage sequences inserted at two different chromosomal sites (attB1 and attB2) following infection with β has been described (Cianciotto et al., 1986). The genome sequence was not available, although the sequence of attB1, but not attB2 had been determined previously (Cianciotto et al., 1990, supra). With this in mind we designed screening primers ATTBu-UP and ATTBu-DN based on the reported attB1 sequence (Table 1). However, it is important to note that in all species in which the sequences of attB1 and attB2 have been determined the identity between these two sites is high, so it is possible that the primers we designed to detect attB1 in *C. ulcerans* may in addition bind at or near attB2. Kanamycin-resistant transformants from matings performed between S17-1/pK-AIM and *C. ulcerans* 712 were screened for attB, attL and attR as described for *C. diphtheriae* and *C. glutamicum*.

In the parental strain *C. ulcerans* 712 we detected a band of the predicted size for attB1 using the primers ATTBu-UP and ATTBu-DN (data not shown). We next used PCR to screen 10 transformants for the presence of the attB1, attL1 or attR1 sites. Six out of 10 strains showed the presence of an attR1 band when screened with ATTBu-DN and ATTP-UP primers (not shown). Strains that lacked this band instead gave an attB1 band when screened with ATTBu-UP and ATTBu-DN:

a site not detected in the six strains that possessed the attR1 site. Thus far the results point to 6 of the transformants arising from an integration event at attB1; and (by implication) to the remaining 4 arising from integration at the un-screened attB2 site. Consistent with this, the six strains possessing attR1 also revealed an attL1 site when screened with ATTBu-UP and ATTP-DN as expected; but in addition the four remaining strains also showed the presence of an attL site when screened with this oligo pair. This result would arise if ATTBu-UP also bound in attB2, as noted in the caveat above, so that the attL2 site would be detected by the same ATTBu-UP/ATTP-DN oligo pair in the PCR screen. In summary, we detected insertions of pK-AIM either at attB1 or attB2, in approximately equal frequencies, in the chromosome of C. ulcerans 712.

Discussion

We describe here the development and use of novel vectors to integrate DNA into the chromosome of C. diphtheriae, C. glutamicum and C. ulcerans. This was accomplished by exploiting the DNA integration functions of a temperate corynephage β. The success of this approach is significant, as relatively few methods have hitherto been described for chromosomal manipulation of *Corynebacterium* species. The system developed here has great utility for characterizing the biochemical events giving rise to pathogenesis and other gene expression pathways in both medically and commercially relevant Coryneform species. In fact this approach requires only a mechanism by which the integrating vector can be delivered to the cytoplasm and a suitable attachment site (a sequence of less than 100 bp) in the bacterial chromosome to mediate insertion so it can be readily adapted for use in a variety of bacterial species. A search of the sequenced genomes available at the National Center for Biotechnology Information (www.ncbi.nlm.nih.gov) revealed attB-like sequences in many bacterial genera including *Tropheryma, Nocardia, Mycobacterium* and *Bacillus* (all with greater than 85% identity over 100 bp) raising the possibility that these vectors might function without adaptation in some of these species.

The tyrosine recombinase family of proteins has been conserved across all three kingdoms of life; and the action of the archetypal lambda integrase protein has been characterized in great detail by many genetic, biochemical, mechanistic and structural studies. The corynephage β integrase and the corresponding att sites, however, have not as yet been studied to the same degree. Nevertheless (at least in terms of the reactions and experiments detailed here) the β system functioned in the same manner as observed with other members of this protein family. While we did not observe any significant differences between the β and β-like integration systems, some mechanistic points relating to the β integrase and att sites are noteworthy, as outlined below.

First, it should be noted that we in fact worked with two very closely related integrase proteins: that from β itself and that of the β-like phage resident in the fully sequenced NCTC13129 isolate—the product of gene DIP0182. Although very similar in sequence and gene order, these two (pro)phages are distinct entities. The two integrase proteins themselves were not identical, with 11 differences across their primary sequences. Vectors with each form of the integrase protein were capable of integration (data not shown), and so clearly either of these integrase proteins can catalyse the site-specific recombination reaction. Thus the 11 differences can be regarded as polymorphisms with no major effect on integrase function. Also of note is that both proteins carry a tyrosine in place of the usually highly conserved histidine 'signature' residue of this protein family. These and other results thus provide strong evidence that the histidine is (despite earlier reports) not completely mandatory for integrase function (Aros et al., 1986, supra; Esposito and Socca, 1997, supra).

Another notable difference between the phage β and β-like sequences relates to genes DIP0180 and DIP0181. These are two small and distinct open reading frames lying between the attL1 site and the DIP0182/int gene in NCTC13129. In β itself, however, using sequencing we observed that these are fused into a single open reading frame as a consequence of the insertion of a single adenine residue in the sequence corresponding to DIP0180 (data not shown). Because β is a viable, infectious phage while NTCT13129 has not been shown to release infectious phage, it is possible that the deletion of the adenine residue to produce DIP0180 and DIP0181 may have caused an inactivation of the phage now resident in NCTC13129 (at least in terms of the lytic cycle). More work will be needed to explore such possibilities.

Bacteriophage attP sites tend to be more extensive than the corresponding attB sites and, apart form the conserved core, carry additional binding sites for proteins that are required for and enhance the integration reaction (Groth and Calos, 2004, J. Mol. Biol. 335, 667-678). Most of the results obtained were with pKMO3W (and derivatives) and these plasmids carry 452 bp of sequence which includes the β attP core. Since the integration reaction functioned efficiently, it is reasonable to assume that all sequences required for recombination at the β attP site reside within this 452 bp region. While this observation may inform the assignment of the full β attP site, the points of strand crossover in the core of the attP and attB sites have yet to be mapped at the nucleotide level. Since exact sequence identity is usually demanded in site-specific recombination crossover regions, it is very likely that this region for the β integrase reaction lies within the 50 bp of shared identity between the β attB and attP sites. Such a location is consistent with a previous study (Michel et al., 1982, J. Virol. 42, 510-518) which mapped the point of strand exchange to within 50 bp of the EcoRI site that lies adjacent to the attB1 core.

The 'minimal' requirements to produce a vector for integrating DNA into Coryneform chromosomes thus seem to be the β integrase gene and some portion of the 452 bp region of attP contained in pKMO3W: no other phage sequences or functions were present on pK-AIM or other vectors that catalyzed integration. The combination of these functions with the oriT mobilization system for DNA transfer, thereby circumventing the relatively impermeable Coryneform cell wall for DNA delivery, yielded a system with many potential applications. For example, the construction of gene deletions in the chromosome of *C. diphtheriae* has been reported by several groups (Ton-That et al., 2004, supra; Schmitt and Drazed, 2001, supra; Oram et al., 2006, supra). This approach, however, is not likely to be successful if an essential gene is to be deleted. One way to overcome this is to first integrate a second copy of the gene of interest into a separate (non-coding) chromosomal locus such as the β attB site(s). The original gene could then be deleted without depriving the cell of the essential function, and a conditional lethal strain could be produced if the complementing gene were subject to stringent regulation by environmental signals that are subject to experimental manipulation.

The vectors developed here also have certain advantages over methods that use pNG2-based replicating plasmids for gene manipulation. These include obviating possible issues arising form the multiplicity and variations in copy number, and the usual requirement for some form of selection to maintain the episome. In fact, while we had previously demonstrated that an intact copy of dtxR was able to reverse the phenotype of the C7(β)ΔdtxR strain when introduced in trans on a replicating plasmid (Oram et al., 2006, supra), this work is the first to establish that a single copy of dtxR integrated into attB2 is capable of restoring DtxR functions to levels seen in a wild-type control. For a more general example, while quantitative real-time reverse transcriptase PCR assays can be used to determine mRNA transcript levels it does not assay directly the regulation that occurs at an individual promoter. Instead, transcriptional fusions of promoters to reporter genes whose activity can be assayed (eliminating the effects of mRNA stability) are routinely used. Promoter activity can now be studied in single copy on the C. diphtheriae chromosome, using the integrating vectors described here as an alternative to placing promoters on an episomal replicating plasmid.

One particularly attractive feature of exploiting the β phage functions is that C. diphtheriae (and several other Coryneform species) possess two β attB sites, allowing for a significant degree of flexibility with this system. Given the link between β lysogeny and diphtheria pathogenesis, it is particularly desirable to have a means to characterize the genetics and biochemical pathways of diphtheria progression. As shown here the C7(β) and NCTC13129 strains, both pathogenic isolates that possess only the attB2 site, were transformed with high efficiency. Thus pathogenic diphtheria strains, despite carrying (usually) one prophage are still perfectly amenable to transformation with this vector. Two separate integrating plasmids could very likely be used (assuming the second one carried a different selection marker than the first) to create two differing and novel integrated sequences. Yet another possibility is that the vector(s) could be used in conjunction with a pNG2-based plasmid (because a pK-AIM-based molecule and a pNG2-based plasmid should not be incompatible.) All these approaches taken together could facilitate the dissection and defined re-construction of significantly complex regulatory and expression gene networks in *C. diphtheriae* and other Corynebacterial species.

What is claimed is:

1. An isolated DNA fragment comprising
   (a) a corynephage integrase gene and
   (b) a corynephage integrase-recognition sequence
wherein said corynephage integrase gene is the int gene set forth in SEQ ID NO: 1 and said corynephage integrase-recognition sequence is attP set forth in SEQ ID NO:2.

2. The DNA fragment of claim 1 further comprising a desired DNA segment to be integrated into a host cell's genome.

3. A vector comprising the DNA fragment of claim 1.

4. The vector of claim 3 wherein said vector is pKMO3W identified as SEQ ID NO:8.

5. The vector of claim 3 further comprising a conjugal origin of transfer.

6. The vector of claim 5 wherein said origin of transfer is oriT.

7. The vector of claim 6 wherein said vector is pKMO3W+ mob identified as SEQ ID NO:9.

8. The vector of claim 6 wherein said vector is pK-AIM identified as SEQ ID NO:10.

9. The vector of claim 4 further comprising a desired DNA segment.

10. The vector of claim 7 further comprising a desired DNA segment.

11. The vector of claim 8 further comprising a desired DNA segment.

12. The vector of claim 11 wherein said DNA segment encodes an antigen.

13. The vector of claim 11 wherein said DNA segment encodes a mutant antigen.

14. The vector of claim 8 further comprising a polylinker.

15. The vector of claim 14 wherein said vector is pK-PIM identified as SEQ ID NO:15.

16. The vector of claim 15 further comprising a desired DNA segment.

17. A host cell transformed with a vector comprising a DNA fragment comprising
   (a) a corynephage integrase gene and
   (b) a corynephage integrase-recognition sequence
wherein the corynephage integrase gene is the int gene set forth in SEQ ID NO: 1 and the corynephage integrase-recognition sequence is attP set forth in SEQ ID NO:2, and
wherein said host cell is selected from the group consisting of corynebacteria, Gram-negative bacteria, Gram-positive bacteria, mycobacteria, plant cell, vertebrate cell, invertebrate cell, and mammalian cell.

18. The host cell of claim 17 wherein said vector further comprises a desired DNA segment.

19. The host cell of claim 18 wherein said DNA segment encodes an antigen.

20. A host cell transformed with the vector of claim 4 wherein said host cell is selected from the group consisting of corynebacteria, Gram-negative bacteria, Gram-positive bacteria, mycobacteria, plant cell, vertebrate cell, invertebrate cell, and mammalian cell.

21. The host cell of claim 20 wherein said vector further comprises a desired DNA segment.

22. A host cell transformed with the vector of claim 8 wherein said host cell is selected from the group consisting of corynebacteria, Gram-negative bacteria, Gram-positive bacteria, mycobacteria, plant cell, vertebrate cell, invertebrate cell, and mammalian cell.

23. The host cell of claim 22 wherein said vector further comprises a desired DNA segment.

24. A host cell transformed with the vector of claim 15 wherein said host cell is selected from the group consisting of corynebacteria, Gram-negative bacteria, Gram-positive bacteria, mycobacteria, plant cell, vertebrate cell, invertebrate cell, and mammalian cell.

25. The host cell of claim 24 wherein said vector further comprises a desired DNA segment.

26. An isolated bacterial cell wherein the DNA fragment of claim 2 is integrated into the genome of the cell.

27. An isolated vertebrate cell wherein the DNA fragment of claim 2 is integrated into the genome of the cell.

28. An isolated mammalian cell wherein the DNA fragment of claim 2 is integrated into the genome of the cell.

29. A method for introducing a desired nucleic acid segment into a corynebacteria comprising
   introducing into the corynebacteria a nucleic acid fragment comprising the nucleic acid fragment of claim 2, such that the integrase catalyzes the integration of the desired nucleic acid fragment in the cell at an attB locus in the corynebacteria.

30. The method of claim 29, wherein introducing the nucleic acid fragment into the cell comprises conjugation.

31. A kit comprising a vector according to claim 4.

32. A kit comprising a vector according to claim 7.

33. A kit comprising a vector according to claim 8.

34. A kit comprising a vector according to claim 15.

35. A host cell transformed with the vector of claim 7 wherein said host cell is selected from the group consisting of corynebacteria, Gram-negative bacteria, Gram-positive bacteria, mycobacteria, plant cell, vertebrate cell, invertebrate cell, and mammalian cell.

36. The host cell of claim 35 wherein said vector further comprises a desired DNA segment.

37. A vector comprising the DNA fragment of claim 2.

* * * * *

UNITED STATES PATENT AND TRADEMARK OFFICE
CERTIFICATE OF CORRECTION

| | | |
|---|---|---|
| PATENT NO. | : 7,892,810 B2 | Page 1 of 1 |
| APPLICATION NO. | : 11/901013 | |
| DATED | : February 22, 2011 | |
| INVENTOR(S) | : Diana Oram, Mark Oram and Joelle Woolston | |

It is certified that error appears in the above-identified patent and that said Letters Patent is hereby corrected as shown below:

In the Specifications:

Column 1, cancel the text in lines 7-9, and insert the following:

-- This invention was made with government support under Grant Number AI060882 awarded by the National Institutes of Health. The government has certain rights in the invention. --

Signed and Sealed this

Nineteenth Day of April, 2011

David J. Kappos
*Director of the United States Patent and Trademark Office*